(12) United States Patent
Yonemitsu et al.

(10) Patent No.: US 8,211,868 B2
(45) Date of Patent: Jul. 3, 2012

(54) PARAMYXOVIRUS VECTOR ENCODING ANGIOGENESIS GENE AND USE THEREOF

(75) Inventors: Yoshikazu Yonemitsu, Fukuoka (JP); Katsuo Sueishi, Fukuoka (JP); Masayuki Fukumura, Ikeda (JP); Xiaogang Hou, Alhambra, CA (US); Mamoru Hasegawa, Tsukuba (JP); Hidenori Matsusaka, Fukuoka (JP); Hiroyuki Tsutsui, Fukuoka (JP)

(73) Assignee: DNAVEC Research Inc., Ibaraki (JP)

( * ) Notice: Subject to any disclaimer, the term of this patent is extended or adjusted under 35 U.S.C. 154(b) by 0 days.

(21) Appl. No.: 13/049,011

(22) Filed: Mar. 16, 2011

(65) Prior Publication Data

US 2011/0212059 A1    Sep. 1, 2011

Related U.S. Application Data

(60) Division of application No. 12/571,196, filed on Sep. 30, 2009, now abandoned, which is a continuation of application No. 10/444,661, filed on May 23, 2003, now abandoned, which is a continuation-in-part of application No. PCT/JP01/10323, filed on Nov. 27, 2001.

(30) Foreign Application Priority Data

Nov. 27, 2000    (JP) .................................. 2000-359374

(51) Int. Cl.
   *A61K 48/00*    (2006.01)
(52) U.S. Cl. ..................................................... 514/44 R
(58) Field of Classification Search .................. 514/44 R
   See application file for complete search history.

(56) References Cited

U.S. PATENT DOCUMENTS

| | | | |
|---|---|---|---|
| 4,994,559 A | 2/1991 | Moscatelli et al. |
| 5,155,214 A | 10/1992 | Baird et al. |
| 6,121,246 A | 9/2000 | Isner |
| 6,274,712 B1 | 8/2001 | Springer et al. |
| 6,645,760 B2 | 11/2003 | Nagai et al. |
| 6,723,532 B2 | 4/2004 | Nagai et al. |
| 7,101,685 B2 | 9/2006 | Nagai et al. |
| 7,226,786 B2 | 6/2007 | Kitazato et al. |
| 7,314,614 B1 | 1/2008 | Yonemitsu et al. |
| 2002/0169306 A1 | 11/2002 | Kitazato et al. |
| 2003/0022376 A1 | 1/2003 | Kitazato et al. |
| 2003/0166252 A1 | 9/2003 | Kitazato et al. |
| 2003/0170210 A1 | 9/2003 | Masaki et al. |
| 2003/0203489 A1 | 10/2003 | Yonemitsu et al. |
| 2004/0005296 A1 | 1/2004 | Yonemitsu et al. |
| 2004/0053877 A1 | 3/2004 | Fukumura et al. |
| 2004/0101965 A1 | 5/2004 | Griesenbach et al. |
| 2005/0266566 A1 | 12/2005 | Nagai et al. |
| 2007/0009949 A1 | 1/2007 | Kitazato et al. |
| 2008/0038234 A1 | 2/2008 | Hayashi et al. |
| 2010/0158867 A1 | 6/2010 | Yonemitsu et al. |

FOREIGN PATENT DOCUMENTS

| | | |
|---|---|---|
| CN | 1407873 A | 4/2003 |
| EP | 0 863 202 A1 | 9/1998 |
| EP | 0 864 645 A1 | 9/1998 |
| EP | 1 179 594 A1 | 2/2002 |
| EP | 1 186 667 A1 | 3/2002 |
| EP | 1 251 174 A1 | 10/2002 |
| EP | 1 291 419 A1 | 3/2003 |
| EP | 1 333 088 A1 | 8/2003 |
| WO | WO 90/02800 | 3/1990 |
| WO | WO 91/09610 | 7/1991 |
| WO | WO 95/25803 | 9/1995 |
| WO | WO 00/70070 | 11/2000 |
| WO | WO 01/32898 A2 | 5/2001 |
| WO | WO 01/32898 A3 | 5/2001 |
| WO | WO 01/41674 | 6/2001 |
| WO | WO 02/38726 A2 | 5/2002 |
| WO | WO 02/38726 A3 | 5/2002 |

OTHER PUBLICATIONS

Asahara et al., "Synergistic Effect of Vascular Endothelial Growth Factor and Basic Fibroblast Growth Factor on Angiogenesis In Vivo," *Circulation* 92(9 Suppl):II365-371, 1995.
Asahara et al., "VEGF Contributes to Postnatal Neovascularization by Mobilizing Bone Marrow-Derived Endothelial Progenitor Cells," *EMBO J.* 18(14):3964-3972, 1999.
Baumgartner et al., "Constitutive Expression of phVEGF$_{165}$ after Intramuscular Gene Transfer Promotes Collateral Vessel Development in Patients with Critical Limb Ischemia," *Circulation* 97(12)1114-1123, 1998.
Burchardt et al., "Expression of Messenger Ribonucleic Acid Splice Variants for Vascular Endothelial Growth Factor in the Penis of Adult Rats and Humans," *Biol. Reprod.* 60(2):398-404, 1999.
Carmeliet, "VEGF Gene Therapy: Stimulating Angiogenesis or Angioma-Genesis?," *Nat. Med.* 6(10):1102-1103, 2000.
Cohen et al., "VEGF$_{121}$, A Vascular Endothelial Growth Factor (VEGF) Isoform Lacking Heparin Binding Ability, Requires Cell-Surface Heparan Sulfates for Efficient Binding to the VEGF Receptors of Human Melanoma Cells," *J. Biol. Chem.* 270(19):11322-11326, 1995.
Couffinhal et al., "Mouse Model of Angiogenesis," *Am. J. Pathol.* 152(6):1667-1679, 1998.
Epstein et al., "Therapeutic Interventions for Enhancing Collateral Development by Administration of Growth Factors: Basic Principles, Early Results and Potential Hazards," *Cardiovasc. Res.* 49(3):532-542, 2001.
Epstein et al., "Angiogenesis Therapy: Amidst the Hype, the Neglected Potential for Serious Side Effects," *Circulation* 104(1):115-119, 2001.
Florkiewicz et al., "Quantitative Export of FGF-2 Occurs Through an Alternative, Energy-Dependent, Non-ER/Golgi Pathway," *J. Cell. Physiol.* 162(3):388-399, 1995.

(Continued)

*Primary Examiner* — J. E. Angell
(74) *Attorney, Agent, or Firm* — Clark & Elbing LLP

(57) ABSTRACT

The present invention provides Paramyxovirus vectors encoding angiogenic genes and use of the same. The use of Paramyxovirus vectors enables effective transfer of angiogenic genes into individual tissues. FGF2 gene transferred into ischemic tissues in vivo induces expression of angiogenic genes without causing edema, and prevents necrosis due to ischemia. The vectors of the present invention are suitable for gene therapy targeted to ischemic tissues.

22 Claims, 14 Drawing Sheets

OTHER PUBLICATIONS

Forsythe et al., "Activation of Vascular Endothelial Growth Factor Gene Transcription by Hypoxia-Inducible Factor 1," *Mol. Cell. Biol.* 16(9):4604-4613, 1996.

Garcia-Martinez et al., "Angiogenesis Induced in Muscle by a Recombinant Adenovirus Expressing Functional Isoforms of Basic Fibroblast Growth Factor," *Gene Ther.* 6(7):1210-1221, 1999.

Hasan et al., "Creation of an Infectious Recombinant Sendai Virus Expressing the Firefly Luciferase Gene from the 3' Proximal First Locus," *J. Gen. Virol.* 78(Pt. 11):2813-2820, 1997.

Hasegawa, "Igaku no Ayumi," 192:237-238, 2000.

Concise explanation of relevance of Hasegawa, "Igaku no Ayumi," 192:237-238, 2000.

Imamura et al., "Recovery of Mitogenic Activity of a Growth Factor Mutant with a Nuclear Translocation Sequence," *Science* 249(4976):1567-1570, 1990.

Isner et al., "Treatment of Thromboangiitis Obliterans (Buerger's Disease) by Intramuscular Gene Transfer of Vascular Endothelial Growth Factor: Preliminary Clinical Results,"*J. Vasc. Surg.* 28(6):964-975, 1998.

Isner, "Tissue Responses to Ischemia: Local and Remote Responses for Preserving Perfusion of Ischemic Muscle," *J. Clin. Invest.* 106(5):615-619, 2000.

Itoh et al., "Intimal Hyperplasia of Experimental Autologous Vein Graft in Hyperlipidemic Rabbits with Poor Distal Runoff," *Atherosclerosis* 110(2):259-270, 1994.

Kalke et al., "Transplantation of Ex Vivo Expanded Endothelial Progenitor Cells for Therapeutic Neovascularization," *Proc. Natl. Acad. Sci. U.S.A.* 97(7):3422-3427, 2000.

Kaneda et al., "Gene Therapy of Cardiovascular Disorders," *Hum. Cell* 12(3):109-114, 1999 (Japanse article with English Abstract).

Kato et al., "Initiation of Sendai Virus Multiplication from Transfected cDNA or RNA with Negative or Positive Sense," *Genes Cells* 1(6):569-579, 1996.

Lederman et al., "Design of the Therapeutic Angiogenesis with Recombinant Fibroblast Growth Factor-2 for Intermittent Claudication (TRAFFIC) Trial," *Am. J.Cardiol.* 88(2):192-195, A6-7, 2001.

Lee et al., "VEGF Gene Delivery to Myocardium: Deleterious Effects of Unregulated Expression," *Circulation* 102(8):898-901, 2000.

Li et al., "A Cytoplasmic RNA Vector Derived from Nontransmissible Sendai Virus with Efficient Gene Transfer and Expression," *J. Virol.* 74(14):6564-6569, 2000.

Masaki et al., "Recombinant Sendai Virus-Mediated Gene Transfer to Vasculature: A New Class of Efficient Gene Transfer Vector to the Vascular System," *FASEB J.* 15(7):1294-1296, 2001.

Masaki et al., "Angiogenic Gene Therapy for Experimental Critical Limb Ischemia: Acceleration of Limb Loss by Overexpression of Vascular Endothelial Growth Factor 165 but not of Fibroblast Growth Factor-2," *Circ. Res.* 90(9):966-973, 2002.

Morinaga et al., "Development and Regression of Intimal Thickening of Arterially Transplanted Autologous Vein Grafts in Dogs," *J. Vasc. Surg.* 5(5):719-730, 1987.

Morishita, "Uehara Kinen Seimei Kagaku-Zaidan Kenkyu Houkokushu," 13:326-327, 1999.

Concise explanation of relevance of Morishita, "Uehara Kinen Seimei Kagaku-Zaidan Kenkyu Houkokushu," 13:326-327, 1999.

Morishita et al., "Therapeutic Angiogenesis Induced by Human Recombinant Hepatocyte Growth Factor in Rabbit Hind Limb lschemia Model as Cytokine Supplement Therapy," *Hypertension* 33(6):1379-1384, 1999.

Murohara et al., "Transplanted Cord Blood-Derived Endothelial Precursor Cells Augment Postnatal Neovascularization," *J. Clin. Invest.* 105(11):1527-1536, 2000.

Nagai, "Paramyxovirus Replication and Pathogenesis. Reverse Genetics Transforms Understanding," *Rev. Med. Virol.* 9(2):83-99, 1999.

Nakanishi et al., "Gene Transfer Vectors Based on Sendai Virus," *J. Control. Release* 54(1):61-68, 1998.

Ogino et al., "Involvement of a Cellular Glycolytic Enzyme, Phosphoglycerate Kinase, in Sendai Virus Transcription," *J.Biol. Chem.* 274(50):35999-36008, 1999.

Onimaru et al., "Fibroblast Growth Factor-2 Gene Transfer Can Stimulate Hepatocyte Growth Factor Expression Irrespective of Hypoxia-Mediated Downregulation in Ischemic Limbs," *Circ. Res.* 91(10):923-930, 2002.

Onimaru et al., "FGF-2-Mediated Hierarchical Regulatory System for Endogenous Expressions of Angiogenesis-Related Factors," *The Journal of Japanese College of Angiology* 46:579-587, 2006 (English Abstract).

Pettersson et al., "Heterogenetiy of the Angiogenic Response Induced in Different Normal Adult Tissues by Vascular Permeability Factor/Vascular Endothelial Growth Factor," *Lab. Invest.* 80(1):99-115, 2000.

Piotrowicz et al., "The 27-kDa Heat Shock Protein Facilitates Basic Fibroblast Growth Factor Release from Endothelial Cells," *J.Biol. Chem.* 272(11):7042-7047, 1997.

Qu et al., "Ultrastructural Immunolocalization of Basic Fibroblast Growth Factor in Mast Cell Secretory Granules. Morphological Evidence for bFGF Release through Degranulation," *J. Histochem. Cytochem.* 46(10):1119-1128, 1998.

Rohan et al., "Genetic Heterogeneity of Angiogenesis in Mice," *FASEB J.* 14(7):871-876, 2000.

Safi, Jr., et al., "Gene therapy with angiogenic factors: a new potential approach to the treatment of ischemic diseases," *J. Mol. Cell. Cardiol.* 29(9):2311-2325, 1997.

Sakai et al., "Accomodation of Foreign Genes into the Sendai Virus Genome: Sizes of Inserted Genes and Viral Replication," *FEBS Lett.* 456(2):221-226, 1999.

Sauter et al., "Adenovirus-Mediated Gene Transfer of Endostatin in Vivo Results in High Level of Transgene Expression and Inhibition of Tumor Growth and Metastases," *Proc. Natl. Acad. Sci. U.S.A.* 97(9):4802-4807, 2000.

Seghezzi et al., "Fibroblast Growth Factor-2 (FGF-2) Induces Vascular Endothelial Growth Factor (VEGF) Expression in the Endothelial Cells of Forming Capillaries: An Autocrine Mechanism Contributing to Angiogensis," *J. Cell Biol.* 141(7):1659-1673, 1998.

Shoji et al., "Intramuscular Gene Transfer of FGF-2 Attenuates Endothelial Dysfunction and Inhibits Intimal Hyperplasia of Vein Grafts in Poor-Runoff Limbs of Rabbit," *Am. J. Physiol. Heart Circ. Physiol.* 285:173-182, 2003.

Shweiki et al., "Vascular Endothelial Growth Factor Induced by Hypoxia May Mediate Hypoxia-Initiated Angiogenesis," *Nature* 359(6398):843-845, 1992.

Springer et al., "VEGF Gene Delivery to Muscle: Potential Role for Vasculogenesis in Adults," *Mol. Cell.* 2(5):549-558, 1998.

Sugihara et al., "A Novel Alternatively Spliced Form of Murine Vascular Endothelial Growth Factor, VEGF 115," *J. Biol. Chem.* 273(5):3033-3038, 1998.

Thurston et al., "Leakage-Resistant Blood Vessels in Mice Transgenically Overexpressing Angiopoietin-1," *Science* 286(5449):2511-2514, 1999.

Thurston et al., "Angiopoietin-1 Protects the Adult Vasculature Against Plasma Leakage," *Nat. Med.* 6(4):460-463, 2000.

Tsutsumi et al., "Essential Role of PDGFRα-p70S6K Signaling in Mesenchymal Cells During Therapeutic and Tumor Angiogenesis in Vivo: Role of PDGFRα During Angiogenesis," *Circ. Res.* 94(9):1186-1194, 2004.

Ylä-Herttuala and Martin, "Cardiovascular Gene Therapy," *Lancet* 355(9199):213-222, 2000.

Yonemitsu et al., "Characterization of in Vivo Gene Transfer into the Arterial Wall Mediated by the Sendai Virus (Hemagglutinating Virus of Japan) Liposomes: An Effective Tool for the in Vivo Study of Arterial Diseases," *Lab. Invest.* 75(3):313-323, 1996.

Yonemitsu et al., "Efficient Gene Transfer to Airway Epithelium Using Recombinant Sendai Virus," *Nat. Biotechnol.* 18(9):970-973, 2000.

Yonemitsu et al., "Nanchisei Kekkanen ni Kansuru Chosa Kenkyuhan, Heisei 11 nendo Kenkyu Houkokushu," 3:58-63, 2000.

Yonemitsu et al., "Angiogenic Factors : Basic Fibroblast Growth Factor (bFGF/FGF-2)," *The Journal of Japanese College of Angiology*, 46:297-304, 2006 (English Abstract).

Yoshimura et al., "FGF-2 Regulation of Neurogenesis in Adult Hippocampus after Brain Injury," *Proc. Acad. Natl. Sci. U.S.A.* 98(10):5874-5879, 2001.

International Search Report for International Application No. PCT/JP01/10323, mailed Mar. 5, 2002.

SEQUENCE LISTING

<160> NUMBER OF SEQ ID NOS: 19

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 1
ctttcaccct                                                              10

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 2
tttttcttac tacgg                                                        15

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 3
cggccgcaga tcttcacg                                                     18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 4
atgcatgccg gcagatga                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 5
gttgagtact gcaagagc                                                     18

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 6

```
tttgccggca tgcatgtttc ccaaggggag agtttttgcaa cc                42
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 7

```
atgcatgccg gcagatga                                           18
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 8

```
tgggtgaatg agagaatcag c                                       21
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 9

```
atgcatatgg tgatgcggtt ttggcagtac                              30
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 10

```
tgccggctat tattacttgt acagctcgtc                              30
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 11

```
gtttaccagg tggagagttt tgcaaccaag cac                          33
```

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 12

```
ctttcacctg gtacaagcac agatcatgga tgg                          33
```

```
<210> SEQ ID NO 13
<211> LENGTH: 84
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 13
atccgcggcc gccaaagttc acttatggca gccgggagca tcaccacgct gcccgccttg       60
cccgaggatg gcggcagcgg cgcc                                              84

<210> SEQ ID NO 14
<211> LENGTH: 82
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 14
atccgcggcc gcgatgaact ttcaccctaa gttttctta ctacggtcag ctcttagcag        60
acattggaag aaaaagtata gc                                                82

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 15
acgtgcggcc gccaaagttc atccaccatg gctgccagcg gcatcacctc gcttccc          57

<210> SEQ ID NO 16
<211> LENGTH: 103
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 16
acgtgcggcc gcgatgaact ttcaccctaa gttttctta ctacgcggat cagctcttag        60
cagacattgg aagaaacagt atggccttct gtccaggtcc cgt                         103

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 17
tgcacccacg acagaagggg a                                                 21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized Primer Sequence
```

-continued

```
<400> SEQUENCE: 18
tcaccgcctt ggcttgtcac at                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 19
ctaccaaaag tttcccaggc ag                                              22
```

PARAMYXOVIRUS VECTOR ENCODING ANGIOGENESIS GENE AND USE THEREOF

CROSS REFERENCE TO RELATED APPLICATIONS

This application is a divisional of U.S. application Ser. No. 12/571,196, filed Sep. 30, 2009, which is a continuation of U.S. application Ser. No. 10/444,661, filed May 23, 2003, which is a continuation-in-part of International Application No. PCT/JP01/10323, filed Nov. 27, 2001, which, in turn, claims the benefit of Japanese Patent Application No. 2000-359374, filed Nov. 27, 2000, the disclosures of which are hereby incorporated by reference.

FIELD OF THE INVENTION

The present invention relates to Paramyxovirus vectors encoding angiogenesis genes and use thereof.

BACKGROUND OF THE INVENTION

Recent research for treatment of ischemic diseases has been performed using growth factors that induce angiogenesis. For example, the therapeutic effect of fibroblast growth factor 2 (FGF2) (Baffour, R. et al., J. Vasc. Surg. 16 (2): 181-91, 1992) and endothelial cell growth factor (ECGF) (Pu, L. Q. et al., J. Surg, Res. 54 (6): 575-83, 1993) on patients with cardiac infarction and acute limb ischemia has been examined. A recent study has revealed that vascular endothelial growth factor (VEGF)/vascular permeability factor (VPF) promotes vasculogenesis in animal models with myocardial ischemia and limb ischemia (Takeshita, S. et al., Circulation 90 (5 Pt 2): 11228-34, 1994; Takeshita, S. et al., J. Clin, Invest. 93 (2): 662-70, 1994).

Clinical trials of human gene therapy using angiogenic growth factors have been undertaken recently. Human gene therapy has been clinically applied to therapeutic angiogenesis in order to treat critical ischemic limb. Vascular endothelial growth factor/vascular permeability factor (VEGF/VPF), an endothelial cell-specific mitogen, is a potent therapeutic gene for this purpose, and it has demonstrated relatively promising results by means of plasmid-based gene transfer involving human subjects (Baumgartner, I., et al., Circulation 97, 1114-1123 (1998); Isner, J. M., et al., J. Vasc. Surg. 28, 964-973 (1998)). However, the related adverse effects and toxicity levels of intramuscular gene transfer of VEGF have been less documented at present because efficiency of plasmid-mediated intramuscular gene transfer and expression are not very high. Since recent reports indicate that transgenic (Thurston, G., et al., Science 286, 2511-2514 (1999)) or adenoviral (Thurston, G., et al., Nature Med. 6, 460-463 (2000)) overexpression of VEGF result in abnormal vasculogenesis in transgene-introduced animals, and that plasmid-based intramuscular VEGF gene transfer showed transient edema in human subjects with ischemic limb (Baumgartner, I., et al., Circulation 97, 1114-1123 (1998); Isner, J. M., et al., J. Vasc. Surg. 28, 964-973 (1998)), detailed mechanisms to cause these pathologies remain to be clarified. Other potential unfavorable effects of VEGF over expression are likely to be the formation of "angioma-like" fragile capillary vessels, possibly due to the imbalance of angiogenic signals (Carmeliet, P., Nature Med. 6, 1102-1103 (2000)). VEGF gene transfer to vessel wall in vivo may cause angiomatousid endothelial proliferation in the severe neointimal formation associating extravasation of red blood cells (Yonemitsu, Y., et al., Lab. Invest. 75, 313-323 (1996)). Similar pathological findings were demonstrated in retrovirus-mediated constitutive overexpression of VEGF in myocardium (Lee, R. J., et al., Circulation 102, 898-901 (2000)). Furthermore, another important issue to be addressed in clinical setting is the level of leakage of locally expressed these angiogenic factors to systemic circulation. Such leakage may cause unexpected angiogenic complications associated with diabetic retinopathy or growth of neoplasm.

Acute critical limb ischemia, which results from acute obstruction of the major arteries, is caused mainly by thrombotic obstruction and is an important target of therapeutic angiogenesis. Acute critical limb ischemia is treated quite unsuccessfully in late interventions, often resulting in limb amputation. Moreover, the long-term prognosis of patients with limb amputation is poor and one-year survival rates of patients after surgery is only 50%. Plasmid-based gene expression levels are low and the efficacy of plasmid-based therapy for acute severe artery occlusion is still unknown.

SUMMARY OF THE INVENTION

An objective of the present invention is to provide Paramyxovirus vectors encoding angiogenic genes and use thereof. More specifically, the present invention provides Paramyxovirus vectors encoding angiogenic genes, angiogenic compositions including the vectors, and methods for promoting angiogenesis in ischemic tissues using the vectors.

Preliminary studies by the present inventors indicated unsuccessful results wherein limb salvage was achieved by means of plasmid-based human VEGF165 gene transfer in mouse model of acute critical limb ischemia (data not shown). To test whether higher expression of transgene may show a better result, the present inventors used recombinant Sendai virus (SeV)-mediated gene transfer, a technique that shows highly efficient gene transfer into various organs. As shown in Examples of this application, the present inventors used two recombinant SeV vectors as therapeutic tools for limb ischemia: one expressing human VEGF165 and the other expressing murine fibroblast growth factor 2 (FGF2). FGF2 (often referred to as bFGF) protein is a growth factor that shows angiogenic effect when administrated (Baffour, R. et al., J. Vasc. Surg. 16: 181-191 (1992)).

Using these vectors, the present inventors analyzed 1) the transgene expression level and kinetics of SeV-mediated intramuscular gene transfer; 2) whether higher expression of angiogenic factors may prevent limb necrosis caused by acute critical limb ischemia or any adverse effects; and 3) whether the higher expression of angiogenic proteins in muscles leads to their leakage into the systemic circulation.

The inventors used ischemic mouse models including BALB/c nu/nu lower limb amputation models (auto-amputation model), in which the entire external iliac artery and vein and femoral artery and vein above the knee were excised (critical ischemia model), and C57BL/6 limb salvage models, which do not lose their lower limbs due to physiological angiogenesis after the same surgical procedures as above. Vectors expressing human VEGF165, mouse FGF2, or luciferase (SeV-hVEGF165, SeV-mFGF2, or SeV-luciferase, respectively) were constructed and administered to thigh and calf muscles two days before ischemia surgery. Lower limbs were observed up to 10 days after surgery.

In the case of luciferase gene transfer into mouse lower limb skeletal muscle, Sev showed 5- to 120-fold higher gene expression levels compared to control plasmid vectors that were administered in an amount of 100 μg (200 mg/60 kg human body weight: corresponding to 25 to 50 fold of the clinical dose). In various cell cultures, both SeV-hVEGF165 and SeV-mFGF2 showed high protein secretion level (50 to 500 ng/$10^5$ cells/24 hours). FGF2 level was increased by 5 to 100 fold by intramuscular administration of SeV-mFGF2 compared with non-administered control (base line). In contrast, the administration of SeV-hVEGF165 caused only limited expression of VEGF in muscle (at most 2 fold above base line) and significantly increased the expression of endogenous VEGF. Widespread necrosis was observed in muscle tissues where SeV-hVEGF165 was administered 2 days after administration and promoted the amputation of lower limbs. On the other hand, SeV-mFGF2 administration showed significant therapeutic effect of limb salvage with an increase in endogenous VEGF expression. In both cases, no significant leakage of vector-derived proteins into the serum was observed (<5 pg/ml). All of the limbs were saved in the non-administered, SeV-luciferase, and SeV-mFGF2 groups, however, one third or more of the SeV-hVEGF group mice in the limb salvage model lost their lower limbs. In the auto-amputation model, only the FGF2 group showed a high limb salvage effect, however, the lower limbs of most of the mice in other groups was auto-amputated.

The present invention revealed that intramuscular administration of recombinant Sendai virus vectors significantly increased transgene expression. Recombinant Sendai virus vectors showed 10- to 100-fold higher expression than plasmid vectors. However, it was found that in vitro administration of recombinant Sendai virus vectors expressing VEGF165 promoted limb amputation in the acute severe ischemia mouse model. Administration of SeV-hVEGF165 induced edema (Example 4, FIG. 8), prevented blood perfusion after ischemic surgery (Example 5, FIGS. 11 and 12), and significantly increased the ratio of limb amputation by ischemia (Example 5, FIGS. 9 and 10). These pathologies would be partly due to strong vascular permeability increasing activity of VEGF. In contrast, administration of Sendai virus expressing FGF2 consistently showed high therapeutic effect. In both models, the fact that no recombinant proteins were detected in the systemic circulatory system, suggests that SeV-mediated FGF2 therapy has little effects to other organs and broad safety regions. These results also indicate that attention must be paid to undesirable effects caused by VEGF in certain limb conditions in human clinical applications. Thus, FGF2 gene therapy, which shows a broad range of safety and therapeutic effect, would be a safe gene therapy system. Furthermore, the present invention demonstrated the effect of SeV vector, which is a potent tool for introducing therapeutic genes in vivo, and enables its use in clinical therapy for acute severe ischemic limb. Moreover, the present inventors performed gene therapy on cardiac infarction model animals using a Sendai virus vector expressing FGF2. Animals were allowed to develop cardiac infraction due to ligature of coronary artery and FGF2-SeV was injected to their myocardium, resulting in an increase in the survival rate compared to individuals to which the control vector was injected. Thus, Paramyxovirus vectors encoding angiogenic genes were confirmed to be effective as gene transfer vectors for ischemic diseases including limb ischemia and myocardiac infarction.

The present invention relates to Paramyxovirus vectors encoding angiogenic genes and use thereof. More specifically, the present invention relates to:

(1) a Paramyxovirus vector encoding an angiogenic gene capable of being expressed;

(2) the Paramyxovirus vector of (1), wherein the angiogenic gene is fibroblast growth factor 2 (FGF2);

(3) the Paramyxovirus vector of (1), wherein the Paramyxovirus is Sendai virus;

(4) the Paramyxovirus vector of (1), wherein said vector lacks the F gene;

(5) an angiogenic composition comprising the Paramyxovirus vector of (1) or a cell containing the vector, and a pharmaceutically acceptable carrier;

(6) an angiogenic composition comprising the Paramyxovirus vector of (2) or a cell containing the vector, and a pharmaceutically acceptable carrier;

(7) an angiogenic composition comprising the Paramyxovirus vector of (3) or a cell containing the vector, and a pharmaceutically acceptable carrier;

(8) an angiogenic composition comprising the Paramyxovirus vector of (4) or a cell containing the vector, and a pharmaceutically acceptable carrier;

(9) a method for inducing angiogenesis, wherein said method comprises the step of administering the angiogenic composition of (5) to a subject in need of angiogenesis;

(10) a method for inducing angiogenesis, wherein said method comprises the step of administering the angiogenic composition of (6) to a subject in need of angiogenesis;

(11) a method for inducing angiogenesis, wherein said method comprises the step of administering the angiogenic composition of (7) to a subject in need of angiogenesis;

(12) a method for inducing angiogenesis, wherein said method comprises the step of administering the angiogenic composition of (8) to a subject in need of angiogenesis;

(13) the method of (9), wherein the angiogenic composition is intramuscularly injected;

(14) a method of treating ischemic tissues, wherein said method comprises the step of administering the angiogenic composition of (5) to a subject in need of angiogenesis, thereby inducing angiogenesis;

(15) a method of treating ischemic tissues, wherein said method comprises the step of administering the angiogenic composition of (6) to a subject in need of angiogenesis;

(16) a method of treating ischemic tissues, wherein said method comprises the step of administering the angiogenic composition of (7) to a subject in need of angiogenesis;

(17) a method of treating ischemic tissues, wherein said method comprises the step of administering the angiogenic composition of (8) to a subject in need of angiogenesis; and

(18) the method of (14), wherein the angiogenic composition is intramuscularly injected.

Using recombinant SeV as a powerful tool for boosting therapeutic genes in muscles, the present inventors characterized in vivo effect of angiogenic factors, VEGF165 and FGF2, for acute severe limb ischemia. Key aspects obtained in this study were; 1) limb ischemia-induced endogenous VEGF rather diffused to systemic circulation than concentrated in muscles and the expression of VEGF165 mediated by the vector of the present invention does not leak significantly to systemic circulation; 2) exogenous FGF2 expression 5- to 100-fold higher than endogenous one did not result in significant systemic diffusion; 3) this level of FGF2 expression also induces endogenous VEGF expression and showed significant limb salvaging effect associating significantly increased limb blood perfusion; and 4) overexpression of VEGF165 apparently induced the limb damage in contrast to that of FGF2. These findings suggest the clinical feasibility of FGF2 with broader safety range as a therapeutic angiogenic factor to treat acute critical limb ischemia. Furthermore, the present inventors are the first to reveal severe adverse effect of VEGF165 gene transfer for limb ischemia.

Interestingly, the present inventors found that limb ischemia-induced endogenous VEGF rather diffused to systemic circulation than concentrated in muscle itself. Although ischemic operation-induced endogenous VEGF expression in muscles and endothelial cells (ECs) was already addressed (Florkiewicz, R. Z. et al., J. Cell. Physiol. 162, 388-399 (1995)), the present inventors are the first to demonstrate that endogenous VEGF seems responsible for the induction of systemic, but not for local, angiogenic response. Asahara et al. showed that systemic administration of VEGF mobilizes endothelial progenitor cells (EPCs) (Asahara, T. et al., EMBO J. 18, 3964-3972 (1999)), suggesting that physiological response to limb ischemia forming collateral vessels is appeared to depend on, to some extent, EPC-mediated "vasculogenesis-like" neovascularization rather than on local angiogenesis by proliferating ECs sprouting from preexisting vessels (Isner J. M., J. Clin. Invest. 106, 615-619 (2000)). Since boosted VEGF in ischemic limb via gene transfer resulted in lack of significant blood perfusion and in limb amputation as demonstrated here, in this case, VEGF may dominantly act as "vascular permeability factor" rather than "angiogenic factor". This may be also supported by the histology of muscles, apparently indicating more extensive intermuscular edema in VEGF165 group.

Secondary, the present inventors showed that PGF2 gene therapy solely is effective to treat ischemic limb, and involves endogenous VEGF function in vivo. Even if the total protein concentration of VEGF in muscle via FGF2 gene transfer was similar to that of VEGF gene transfer, FGF2 gene therapy itself, but not VEGF, was sufficiently effective. These findings suggest that not only VEGF but also FGF2 may be necessary to form mature blood vessels for therapeutically perfusing blood to ischemic limbs and to prevent vascular leakage. Furthermore, angiopoietin-1, an angiogenic factor that prevents vascular leakage of VEGF-induced immature vessels, may contribute to this.

The reason why injection of SeV-VEGF165 could not show comparable expression to SeV-FGF2 or SeV-luciferase in muscle in vivo is not still fully addressed because SeV-VEGF165 works in vitro sufficiently to secrete gene product similar to SeV-FGF2. Similar to histological study, laser Doppler perfusion imaging (LDPI) showed extensively damaged muscular tissue with lack of blood perfusion. Thus, it may be possible that cellular machinery of SeV-mediated transcription including tubulin (Moyer, S. A., et al., Proc. Natl. Acad. Sci. USA 83, 5405-5409 (1986)) and phosphoglycerate kinase (Ogino, T., et al., J. Biol. Chem. 274, 35999-36008 (1999)), may be disturbed or altered due to edema caused by VEGF165-induced tissue damage. Inversely, relatively low level of exogenous VEGF165 gene expression markedly enhanced endogenous VEGF (approximately 200 pg/g muscle) in severely ischemic muscles (1,400 pg/g muscle), resulting in accelerated limb amputation. These results strongly suggest that enhanced concentration of VEGF in muscle, even if it is relatively low and around 2-hold higher than the baseline, can lead limbs to critical limb ischemia.

Angiogenesis is considered as a well-harmonized process and a lot of factors may be involved. Among these factors, the biological function of VEGF is highly dose-dependent, resulting in fatal defect even with single loss of allele (Carmeliet, P. et al., Nature 380, 435-439 (1996)). Constitutive VEGF expression is necessary during entire process of vascular integrity and maturation, because transient VEGF expression only induces short-lived angiogenic responses (Pettersson, A. et al., Lab. Invest. 80, 99-115 (2000)), and further, VEGF-induced capillary-like structure rarely makes connections to preexisting blood vessels (Springer, M. L., et al., Mol. Cell. 2, 549-558 (1998)). Thus, the present invention suggests that more than 2-fold higher concentration of VEGF in muscle without sufficient FGF2 is likely to be seriously toxic. Considering these, more careful attention than ever should be paid in use of VEGF for therapeutic angiogenesis, although VEGF still holds great clinical potential. Furthermore, intramuscular FGF2 gene transfer was demonstrated to be safe and significantly therapeutically effective for limb salvage in acute severe limb ischemia cases.

Herein, a "Paramyxovirus vector" is defined as a vector (or carrier) that is derived from the Paramyxovirus and that is used for gene transfer to host cells. The Paramyxovirus vector of the present invention may be ribonucleoprotein (RNP) or a virus particle having infectivity. Herein, the term "infectivity" is defined as an ability of the recombinant Paramyxovirus vector to transfer, through its cell adhesion and membrane fusion abilities, a gene contained in the vector to cells to which the vector is adhered. The Paramyxovirus vector of the present invention may have replication ability, or may be a defective vector without the replication ability. Herein, "replication ability" is defined as the ability of virus vectors to replicate and produce infective virus particles in host cells infected with the virus vectors. The replication ability can be determined using, for example, monkey kidney-derived cell line, LLC-MK2 or CV-1.

Herein, a "recombinant" Paramyxovirus vector is defined as a Paramyxovirus vector constructed by gene engineering or its amplified products. For instance, recombinant Paramyxovirus vectors can be generated by reconstitution of a recombinant Paramyxovirus cDNA.

Herein, a Paramyxovirus is defined as a virus of the Paramyxoviridae family or a derivative thereof. Paramyxoviruses used in the present invention include, for example, viruses belonging to the Paramyxoviridae such as Sendai virus, Newcastle disease virus, Mumps virus, Measles virus, Respiratory syncytial virus, rinderpest virus, distemper virus, simian parainfluenza virus (SV5), and type I, II, and III human parainfluenza virus. The virus of the present invention may be preferably a virus of the genus Paramyxovirus or a derivative thereof. Paramyxovirus that can be used in the present invention includes, for example, type I human parainfluenza virus (HPIV-1), type III human parainfluenza virus (HPIV-3), type III bovine parainfluenza virus (BPIV-3), Sendai virus (also referred to as "type I mouse parainfluenza virus"), type X simian parainfluenza virus (SPIV-10), etc. Most preferable Paramyxovirus of the invention is Sendai virus. These viruses may be naturally occurring, wild-type, mutant, laboratory-passaged, artificially constructed strains, etc. Incomplete viruses such as the DI particle (Willenbrink W. and Neubert W. J., J. Virol., 1994, 68, 8413-8417) and synthesized oligonucleotides may also be utilized as a material for generating the virus vector of the present invention.

Genes encoding proteins of a Paramyxovirus include NP, P, M, F, HN, and L genes. Herein, the "NP, P, M, F, HN, and L genes" represent those encoding the nucleocapsid protein, phosphoprotein, matrix protein, fusion protein, hemagglutinin-neuraminidase, and large protein, respectively. Genes of each virus of the subfamily Paramyxovirus are described generally as follows. In general, NP gene may also be indicated as "N gene".

| Paramyxovirus | NP | P/C/V | M | F | HN | — | L |
|---|---|---|---|---|---|---|---|
| Rublavirus | NP | P/V | M | F | HN | (SH) | L |
| Morbillivirus | NP | P/C/V | M | F | H | — | L |

For instance, the accession numbers of each gene of the Sendai virus classified as a Respirovirus of Paramyxoviridae in the nucleotide sequence database, are M29343, M30202, M30203, M30204, M51331, M55565, M69046, and X17218 for NP gene; M30202, M30203, M30204, M55565, M69046, X00583, X17007, and X17008 for P gene; D11446, K02742, M30202, M30203, M30204, M69046, U31956, X00584, and X53056 for M gene; D00152, D11446, D17334, D17335, M30202, M30203, M30204, M69046, X00152, and X02131 for F gene; D26475, M12397, M30202, M30203, M30204, M69046, X00586, X02808, and X56131 for HN gene; and D00053, M30202, M30203, M30204, M69040, X00587, and X58886 for L gene.

As used herein, the term "gene" refers to a genetic substance, including nucleic acids such as RNA and DNA, which may or may not encode a protein. A gene may encode a functional RNA such as ribozyme or antisense RNA. It can be a naturally occurring sequence or an artificially designed sequence. Furthermore, as used herein, the term "DNA" includes a single-stranded DNA and a double-stranded DNA.

The present invention provides a Paramyxovirus vector encoding angiogenic gene and use of the same. The present inventors showed that transgene expression was increased at the administered sites where a Paramyxovirus vector encoding an angiogenic gene was administrated intramuscularly in vivo. The present inventors revealed that necrosis in ischemic tissues could be prevented by the administration of a recombinant Paramyxovirus vector encoding an angiogic gene (FGF2) and loss of the hind limb could be prevented in a limb salvage experiment using mice with ischemic hind limbs. Moreover, the Paramyxovirus vector is effective in gene therapy for ischemic heart. Vectors of this invention are useful in effectively inducing angiogenesis in ischemic tissues and in preventing necrosis, and can thus be preferably used for gene therapy for ischemic diseases.

Moreover, the present inventors revealed that genes administered intramusculary using recombinant Paramyxovirus vectors could be continuously expressed for 1 to 2 weeks. This result indicates that gene therapy with angiogenic factors using recombinant Paramyxovirus vectors can achieve continuous therapeutic effects. Moreover, angiogenic factors expressed from recombinant Paramyxovirus vectors administered intramuscularly could not be detected in the systemic circulatory system and, thus, would not cause undesirable effects outside of the target tissues. Therefore, the findings of the present invention that Paramyxovirus vectors have various benefits in angiogenic gene transfer suggest possible great improvement in gene therapy by specifically targeting ischemic tissues.

Since Paramyxovirus vectors are not pathogenic in humans, they can be suggested to be preferably utilized in clinical trials of human gene therapy in view of safety. It is a major obstacle in high efficient gene transfer that, in most cases, introduced DNA must be transported into the nucleus or nuclear membrane must be eliminated for the expression of an exogenous gene via plasmid DNA or such. In the case of Sendai virus, however, expression of an exogenous gene is driven by both cellular tubulin and its RNA polymerase (L protein) in the cytoplasm when viruses replicate. This suggests that the Sendai virus does not interact with chromosomes of host cells, which avoids risks such as cancerization and immortalization of cells. Furthermore, the Sendai virus is known to be pathogenic in rodents causing pneumonia, but not in humans, which is supported by studies showing that the intranasal administration of the wild type Sendai virus does not do harm in nonhuman primates (Hurwitz J. L. et al., Vaccine, 1997, 15, 533-540). These features suggest that Sendai virus vector can be utilized in human therapy, and further, support the notion that Sendai virus vectors can be one of the promising tools in gene therapy with angiogenic genes.

Angiogenic genes used herein indicate genes encoding factors, which have activities to promote angiogenesis and/or vasculogenesis directly or indirectly. The factors can be proteins or peptides, or can be nucleic acids such as functional RNAs (ribozymes or antisense RNAs). Angiogenic proteins include, for example, acidic fibroblast growth factor (aFGF), fibroblast growth factor 2 (FGF2) (also called basic fibroblast growth factor (bFGF)), vascular endothelial growth factor (VEGF), angiopoietins (Ang) (including Ang-1 and Ang-2), epidermal growth factor (EGF), transforming growth factor-$\alpha$ (TGF-$\alpha$), TGF-$\beta$, platelet-derived endothelial cell growth factor (PD-ECGF), platelet-derived growth factor (PDGF), tumor necrosis factor-$\alpha$ (TNF-$\alpha$), hepatocyte growth factor (HGF), insulin-like growth factor (IGF), erythropoietin (EPO), colony-stimulating factor (CSF), macrophage colony-stimulating factor (M-CSF), granulocyte-macrophage colony-stimulating factor (GM-CSF), interleukin (IL)-8, and nitric oxide synthetase (NOS) (Klagsbrun, M. and D' Amore, P., A. Annu. Rev. Physiol. 53: 217-39, 1991; Folkman, J. and Shing, Y., J. Biol. Chem. 267 (16): 10931-4, 1992; Symes, J. F. and Sniderman, A. D., Curr. Opin. Lipidol. 5 (4): 305-12, 1994).

The preferred angiogenic proteins in the present invention include, for example, aFGF, FGF2, Ang-1, Ang-2, EGF, TGF-$\alpha$, TGF-$\beta$, PD-ECGF, PDGF, TNF-$\alpha$, HGF, IGF, EPO, CSF, M-CSF, GM-CSF, IL-8, and NOS, and the vectors can be constructed using genes encoding the proteins selected from the list above.

Proteins especially preferred among angiogenic proteins used in the present invention are not those which induce premature angiogenesis by VEGF, but those which achieve angiogenesis in which blood vessel is surrounded by parietal cells that are differentiated from the newly generated endothelial cells attached to mesenchymal cells. It is known that vascularization consists of three steps, vasculogenesis, angiogenesis, and vascular maturation. Observations of various transcription factor-knockout studies revealed that maturation in vascularization involves multiple genes. Specifically, transcription factor SCL/tal-1 is mainly involved in vascular formation, and HIF-1, Id, ETS-1, HOXD$_3$, COUP-TFII, and MEF2C are involved in angiogenesis. Furthermore, it is known that lung kruppel-like factor (LKLF) or dHAND gene knock out causes embryonic death due to undeveloped parietal cells.

Therefore, angiogenic genes used in the present invention are, more preferably, those that induce transcription factors, including LKLF and dHAND, involved in parietal cell maturation in premature mesenchymal cells. It is predicted that FGF2 stimulation is directly involved in the induction of these transcription factors or promotes proliferation and differentiation of mesenchymal cells through other growth factors such as angiopoietin and HGF.

Angiogenic proteins preferably contain secretion signal sequences that allow the secretion of the angiogenic proteins. However, proteins, such as FGF2 can be secreted outside of cells without a native and typical secretion signal sequence (see Example). These proteins do not necessarily require secretion signal sequences. The genes encoding these angiogenic proteins, for example, can be obtained by known methods, such as PCR using primers, which are designed, based on the nucleotide sequence information. An example of the most preferred angiogenic factor used in the present invention is FGF2, which shows a stable therapeutic effect in a wide range of expression levels. (Abraham, J. A. et al., 1986, EMBO J. 5: 2523-2528; Moscatelli, D. A. et al., U.S. Pat. No. 4,994,559; Baird, A. et al., U.S. Pat. No. 5,155,214; Isner, J. M. U.S. Pat. No. 6,121,246; WO 97/14307).

Angiogenic genes used for vector construction can be heterologous or homologous to, preferably homologous to, the target individuals for gene transfer in order to achieve a desired effect. Furthermore, angiogenic genes used for vector construction are preferably mammalian angiogenic genes, preferably human genes for application to human.

Paramyxovirus vectors encoding angiogenic genes of the present invention is especially effective for the treatment of ischemic tissues. Namely, gene transfer of angiogenic genes using the vectors of the present invention can promote angiogenesis and prevent necrosis due to ischemia. The ischemic tissues used for the present invention are not limited so long as the tissues show ischemia or are developing ischemia. For example, such tissues include muscle, brain, kidney, and lung. The ischemic diseases treated by administering vectors of the present invention include cerebrovascular ischemia, kidney ischemia, lung ischemia, limb ischemia, ischemic cardiomyopathy, and myocardial ischemia. Treatment of ischemic tissues in the present invention includes therapy of ischemic tissues or prevention of ischemic obstruction, specifically, for example, prevention of necrosis in ischemic tissues, sustaining ischemic tissues, promotion of angiogenesis in ischemic tissues, tissue regeneration, and preventing and decreasing obstruction caused by ischemia.

The present invention provides methods for inducing angiogenesis, which comprises the step of administering Paramyxovirus vectors encoding angiogenic genes. Moreover, the present invention provides methods for treating ischemic tissues, which comprises the step of administering Paramyxovirus vector encoding angiogenic gene. There is no limitation to the target individuals and, for example, a desirable mammal including a human can be used. In particular, non-human mammals, such as primates including monkeys such as prosimian, platyrrhine monkeys, and catarrhine monkeys, apes of anthropoid, rodents such as mice, rats, and guinea pigs, as well as cows, dogs, cats, horses, sheep, and rabbits can be targets for administration. It is possible to treat ischemia in the animals using vectors of the present invention and also possible to use the animals as ischemia therapy models for humans (Morinaga, K. et al., 1987, J. Vasc. Surg. 5: 719-730; Itoh, H. et al., 1994, Atherosclerosis 110: 259-270).

Specific methods for inducing angiogenesis according to the present invention include the following methods: a] a method for inducing angiogenesis, which comprises the step of administering a Paramyxovirus vector encoding an angiogenic gene or a cell containing the vector;
[b] the method of [a], in which the angiogenic gene is fibroblast growth factor 2 (FGF2);
[c] the method of [a] or [b], in which the gene is administered intramuscularly; and
[d] the method of any one of [a] to [c], in which the Paramyxovirus is Sendai virus.

Examples of the methods for treating the ischemic tissues in the present invention include the following methods:
[a] a method for treating the ischemic tissues, which comprises the step of administering a Paramyxovirus vector encoding an angiogenic gene or a cell containing the vector;
[b] the method of [a], in which the angiogenic gene is fibroblast growth factor 2 (FGF2);
[c] the method of [a] or [b], in which the gene is administered intramuscularly; and
[d] the method of any one of [a] to [c], in which the Paramyxovirus is Sendai virus.

Administration can be carried out either in vivo or ex vivo. For in vivo administration, Paramyxovirus vectors encoding angiogenic genes can be injected via administration routes well known to those skilled in the art such as intramuscular injection, subcutaneous injection, and catheter administration. For ex vivo administration, the vectors are used to pretransfect cells in vitro. The cells containing the vectors are then injected in vivo by methods such as intramuscular injection, subcutaneous injection, and catheter administration. The cells for transferring vectors in ex vivo administration can be either heterologous or homologous to the target individuals, but are preferably homologous thereto. Cells derived from the target individual are more preferable. Moreover, the cells are most preferably derived from bone marrow or blood, including cells which can form vascular endothelial cells or which can be differentiated into vascular endothelial cells, that is, vascular endothelial progenitor cells. Angiogenesis can be induced in target tissues into which a pharmaceutically effective dose of a vector of the present invention is administered. Therefore, it is possible to perform treatment for preventing tissue necrosis and limb amputation in, for example, ischemic brains, hearts, kidneys, lungs, and limbs.

Furthermore, the present invention provides Paramyxovirus vectors encoding angiogenic genes to treat ischemic tissues. Specifically, the present invention provides:
[a] a Paramyxovirus vector encoding an angiogenic gene for treating an ischemic tissue;
[b] the vector of [a], in which the angiogenic gene is fibroblast growth factor 2 (FGF2);
[c] the vector of [a] or [b], in which the vector is used for intramuscular administration; and
[d] the vector of any one of [a] to [c], in which Paramyxovirus is Sendai virus.

Moreover, the present invention provides compositions, comprising Paramyxovirus vectors for treating ischemic tissues: The compositions can include pharmaceutically acceptable carriers in addition to Paramyxovirus vectors. For example, the vectors of the present invention can be formulated into injections with physiological solutions or into implants with solid or semisolid (gel) materials.

Paramyxovirus vectors used for angiogenic gene transfer according to the present invention is not particularly limited. For instance, preferable Paramyxovirus vectors include vectors that are able to replicate and autonomously proliferate. In general, for example, the genome of wild type Paramyxoviruses contain a short 3' leader region followed by six genes, encoding nucleocapsid (N), phospho (P), matrix (M), fusion (F), hemagglutinin-neuraminidase (HN), and large (L) proteins, and has a short 5' trailer region on the other terminus. Vectors of the present invention that are able to replicate autonomously can be obtained by designing a genome having a similar structure to that as described above. In addition, a vector for expressing an exogenous gene can be obtained by inserting an exogenous gene to the genome of the above vector. Paramyxovirus vectors of the invention may have an altered alignment of virus genes, compared with wild type viruses.

Paramyxovirus vectors of the present invention may have any deletion of the genes that are contained in the wild-type Paramyxovirus. For instance, when Sendai virus vectors are reconstituted, proteins encoded by NP, P/C, and L genes are thought to be required in trans, but the genes themselves may not be a component of virus vectors of the present invention. For example, an expression vector carrying genes encoding the proteins may be co-transfected into host cells with another expression vector encoding the vector genome to reconstitute a vector. Alternatively, an expression vector encoding the virus genome is introduced into host cells carrying genes encoding the proteins, and then the vector can be reconstituted by using the proteins derived from the host cell. The amino acid sequence of these proteins may not be identical to those derived from the original virus as long as it has an equivalent or higher activity in nucleic acid transfer, and may be mutated or replaced with that of a homologous gene of another virus.

Proteins encoded by M, F, and HN genes are thought to be essential for cell-to-cell propagation of a Paramyxovirus vector. However, these proteins are not required when a Paramyxovirus vector is prepared as RNP. If genes M, F, and HN are components of the genome contained in RNP, products of these genes are produced when introduced into host cells, and virus particles having infectivity are generated. RNP vectors that produce an infective virus include, for example, a viral genomic RNA encoding N, P, M, F, HN, and L genes and N, P, and L proteins. When such RNP is introduced into cells, virus genome is expressed and replicated through functions of N, P, and L proteins, and thus infective virus vectors are amplified.

RNP can be introduced into cells as a complex with, for example, lipofectamine and polycationic liposome. Specifically, a variety of transfection reagents can be used, for instance, DOTMA (Boehringer), Superfect (QIAGEN #301305), DOTAP, DOPE, and DOSPER (Boehringer #1811169). Chloroquine may be added to prevent degradation in the endosome (Calos M. P., Proc. Natl. Acad. Sci. USA, 1983, 80, 3015). For replicative viruses, the produced viruses can be amplified or passaged by re-infecting into cultured cells, chicken eggs, or animals (e.g. mammalian such as mice).

Paramyxovirus vectors lacking the M, F, and/or HN genes are also used preferably as Paramyxovirus vectors of the present invention. These virus vectors can be reconstituted by providing deleted gene products exogenously. Such vectors can still adhere to host cells and induce cell fusion like the wild-type virus. However, daughter virus particles do not have the same infectivity as the parent ones because the vector genome introduced into cells lacks one or more of these genes. Therefore, these vectors can be useful as safe virus vectors that are capable of only a single gene transfer. Specifically, genes deleted from the genome may be F and/or HN genes. "Gene-deficient" is defined as substantial loss of gene function, and, when a deficient gene encodes a protein, the gene-deficient mutant does not express any protein having a function equivalent to the wild type protein. For example, being deficient in one or more genes can be achieved by no transcription of the gene(s), loss-of-function mutants, and deletin of the genes. Gene-deficient means that, preferably, at least a part of the coding region, more preferably, the entire coding region of the gene is deficient. For example, F gene-deficient vectors are vectors deficient in, preferably, a part of the F protein-coding region, more preferably, the entire F protein-coding region. Still more preferably, F gene-deficient vectors of the present invention lack the start signal sequence in the 3' flanking site of the F gene, which is deficient in the negative chain in the genome. Therefore, unnecessary polypeptides expression from the deficient area can be suppressed. When the open reading frame (ORF) encoding unnecessary polypeptides exist in the deficient region, it is desirable to remove the ORF by methods such as site-directed mutagenesis (described later).

For preparing F gene-deficient vectors, virus vectors can be reconstituted by co-transfection of an expression plasmid encoding the genome of a recombinant Paramyxovirus lacking the F gene, with an expression vector for the F protein, and that for NP, P/C, and L proteins into host cells (International Publication numbers WO 00/70055 and WO 00/70070). Alternatively, host cells in which the F gene is integrated into the chromosome may be used. The amino acid sequence of these proteins provided exogenously may not be identical to those of the wild type and may be mutated or replaced by a homologous protein of another virus as long as they provide equivalent or higher gene transfer activity.

The envelope protein of Paramyxovirus vectors of the invention may contain another protein than the envelope protein of the original vector genome. There is no limitation on such proteins. These include envelope proteins of other viruses such as the G protein (VSV-G) of the vesicular stomatitis virus (VSV). Thus, Paramyxovirus vectors of the invention include a pseudo-type virus vector that has an envelope protein derived from a virus different from the original virus.

Paramyxoviral vectors of the present invention may also comprise, for example, on the viral envelop surface, proteins capable of adhering to particular cells, such as adhesion factors, ligands and receptors or chimeric proteins comprising a protein described above on the outer surface and viral envelop-derived polypeptides inside the virus. It enables the production of a vector targeting a particular tissue. These proteins may be encoded by the virus genome itself, or supplied at the time of virus reconstitution through expression of genes other than virus genome (for example, genes derived from another expression vector or host cell chromosome).

The virus genes contained in the vector of the present invention may be altered, for example, to reduce antigenicity or enhance RNA transcription efficiency or replication efficiency. Specifically, it is possible to alter at least one of the NP, P/C, and L genes, which are genes of replication factors, to enhance transcription or replication. It is also possible to alter the HN protein, a structural protein having hemagglutinin activity and neuraminidase activity, to enhance the virus stability in blood by weakening the former activity and to regulate infectivity by altering the latter activity. It is also possible to alter the F protein, which is implicated in membrane fusion, to regulate its fusion ability. Furthermore, it is possible to analyze the antigen presenting epitopes and such of possible antigenic molecules on the cell surface such as the F protein and HN protein and use them to generate a Paramyxovirus vector that is engineered to have weak antigen presenting ability.

Paramyxovirus vectors of the present invention may also lack accessory genes. For example, the disruption of the V gene, one of the accessory genes of SeV, results in reduction of pathogenicity of SeV toward hosts such as mouse without affecting gene expression and replication in cultured cells (Kato, A. et al. 1997. J. Virol. 71:7266-7272; Kato, A. et al. 1997. EMBO J. 16:578-587; Curran, J. et al., WO 01/04272, EP 1067179). Such attenuated vectors are particularly suitable as in vivo or ex vivo gene transfer vectors.

Viral vectors of the present invention encode angiogenic genes in its genomic RNA. Recombinant Paramyxovirus vector comprising exogenous genes can be prepared by inserting exogenous genes into the above-mentioned Paramyxovirus vector genome. An exogenous gene can be a desired angiogenic gene to be expressed in target tissues, such as ischemic tissues, for vector transfer. The exogenous gene may encode a naturally occurring protein, or a modified protein prepared by modifying the original protein by deletion, substitution, or insertion, as long as the modified protein is functionally equivalent to the naturally occurring protein. For instance, for the purpose of gene therapy and such, a gene used to treat a target disease may be inserted into the DNA (virus vector DNA) encoding the genome of the virus vector. In the case of inserting an exogenous gene into virus vector DNA, such as Sendai virus vector DNA, a sequence comprising nucleotides of multiples of six is desirably inserted between the transcription end sequence (E) and the transcription start sequence (S) (Calain P. and Roux L., J. Virol., 1993, 67(8), 4822-4830). An exogenous gene can be inserted upstream and/or downstream of each of the virus genes (NP, P, M, F, HN, and L genes). In order not to interfere with the expression of upstream and downstream genes, an E-I-S sequence (transcription end sequence-intervening sequence-transcription start sequence) or a portion of it may be suitably placed upstream or downstream of an exogenous gene so that E-I-S sequence is located between each gene. Alternatively, an exogenous gene can be inserted via IRES sequence.

Expression level of inserted exogenous genes can be regulated by the type of transcription start sequence that is attached to the upstream of the genes (WO 01/18223). It also can be regulated by the position of insertion and the sequence surrounding the gene. In the Sendai virus, for instance, the closer to the 3'-terminus of the negative strand RNA of the virus genome (the closer to NP gene in the gene arrangement on the wild type virus genome) the insertion position is, the higher the expression level of the inserted gene will be. To achieve a high expression of an exogenous gene, it is preferably inserted into the upstream region of the negative stranded genome such as the upstream of the NP gene (3' flanking sequence on the negative strand), or between NP and P genes. Conversely, the closer to the 5'-terminus of the negative strand RNA (the closer to L gene in the gene arrangement on the wild type virus genome) the insertion position is, the lower the expression level of the inserted gene will be. To reduce the expression of an exogenous gene, it may be inserted into the most 5' position on the negative strand, that is, downstream of the L gene in the wild type virus genome (5' flanking region of the L gene on the negative strand) or upstream of the L gene (3' flanking region of L gene on the negative strand). Thus, the insertion position of an exogenous gene can be properly adjusted to obtain a desired expression level of the gene or optimize the combination of the insert with the virus genes surrounding it. For instance, if the overexpression of an angiogenic gene introduced by a high-titer virus vector may cause toxicity, it is possible not only to control the titer of viruses to be administered but also to reduce the expression level of individual virus vectors by designing the insertion position of the angiogenic gene closer to the 5'-terminus of the negative strand, or replacing the transcription start sequence with one having lower efficiency so as to obtain an appropriate effect.

To help the easy insertion of an exogenous gene, a cloning site may be designed at the position of insertion. For example, the cloning site may be the recognition sequence of restriction enzymes. The restriction sites in the vector DNA encoding viral genome can be used to insert an exogenous gene. The cloning site may be a multicloning site that contains recognition sequences for multiple restriction enzymes. The vector of the present invention may have other exogenous genes at positions other than that used for above insertion. Such exogenous gene may be, without limitation, an angiogenic gene or another gene.

Construction of a recombinant Sendai virus vector having an exogenous gene can be performed as follows, for example, according to the method described in Hasan, M. K. et al., J. Gen. Virol., 1997, 78: 2813-2820, Kato A. et al., EMBO J., 1997, 16: 578-587, and Yu D. et al., Genes Cells, 1997, 2: 457-466.

First, a DNA sample containing a cDNA nucleotide sequence encoding a desired exogenous gene is prepared. It is preferable that the concentration of the DNA sample is 25 ng/μl or higher and that it can be detected as a single plasmid by electrophoresis. The following description is an example where an exogenous gene is inserted into the NotI site of virus genomic DNA. If the target cDNA sequence contains a NotI recognition site, the site is desirably removed in advance by altering the nucleotide sequence using the known method such as site-directed mutagenesis while maintaining the encoded amino acid sequence. A desired DNA fragment is amplified by PCR from the DNA sample. In order to obtain a fragment having NotI sites at both ends and to add a single copy of the transcription end sequence (E), intervening sequence (I), and transcription start sequence (S) of the Sendai virus (EIS sequence) to one end, synthesized DNA sequences (primer pair), namely, a pair of a forward primer (sense strand) comprising a part of the desired gene, and a reverse primer (antisense) comprising a NotI recognition site, E, I, and S sequences, and part of the desired gene, is prepared.

For example, the forward synthetic DNA sequence contains two or more nucleotides at the 5'-terminus to ensure digestion with NotI (preferably 4 nucleotides not containing a sequence derived from the NotI recognition site, such as GCG and GCC; more preferably ACTT). To the 3'-terminus of the sequence, the NotI recognition sequence GCGGCCGC is added. Furthermore, to the 3'-terminus, as a spacer, any 9 nucleotides or those of 9 plus multiples of 6 are added. Furthermore, to the 3'-terminus, a sequence of approximately 25 nucleotides corresponding to the ORF of the desired cDNA starting from the initiation codon ATG is added. The 3'-terminus of the forward synthetic oligo DNA containing approximately 25 nucleotides of the desired cDNA is preferably selected so that the last nucleotide is G or C.

The reverse synthetic DNA sequence contains two or more nucleotides at the 5'-terminus (preferably 4 nucleotides not containing a sequence derived from the NotI recognition site, such as GCG and GCC; more preferably ACTT). To the 3'-terminus of the sequence, the NotI recognition sequence GCGGCCGC is added. Furthermore, to the 3'-terminus, a spacer oligo DNA is added to adjust the length of the primer. The length of the oligo DNA is designed so that it is a multiple of 6 nucleotides including the NotI recognition sequence GCGGCCGC, the sequence complementary to the cDNA, and the EIS sequence derived from the Sendai virus genome as described below (so-called "rule of six"; Kolakofski D. et al., J. Viral., 1998, 72, 891-899; Calain P. and Roux L., J. Viral., 1993, 67, 4822-4830). Furthermore, to the 3'-terminus of the added sequence, complementary sequences to the S sequence of the Sendai virus, preferably 5'-CTTTCACCCT-3' (SEQ ID NO: 1), to the I sequence, preferably 5'-AAG-3', and to the E sequence, preferably 5'-TTTTTCTTACTACGG-3' (SEQ ID NO: 2) are added. Finally, to the 3'-terminus, a sequence, which is selected so that the last nucleotide of the complementary sequence of the desired cDNA becomes G or C, is added, where the last nucleotide is approximately 25 nucleotides upstream from the termination codon. Thus, the 3'-terminus of the reverse synthetic oligo DNA is prepared.

PCR can be performed by a common method using, for example, ExTaq polymerase (TaKaRa). Vent polymerase (NEB) may be used preferably, and the amplified fragment is digested with NotI, and inserted into the NotI site of the plasmid vector pBluescript. The nucleotide sequence of the obtained PCR product is checked with an automated DNA sequencer, and a plasmid having the correct sequence is selected. The insert is excised from the plasmid by NotI digestion, and subcloned into the NotI site of the plasmid comprising Paramyxovirus genomic cDNA. Alternatively, the PCR products may be directly cloned into the NotI site without using pBluescript plasmid vector to obtain recombinant Sendai virus cDNA.

For example, recombinant Sendai virus genomic cDNA can be constructed according to the methods described in literatures (Kato; A. et al., EMBO J. 16: 578-598, 1997; Hasan, M. K. et al., J. Gen. Virol., 78: 2813-2820, 199.7; Yu, D. et al., Genes Cells, 1997, 2, 457-466; and Li, H. O. et al., J. Virology 74, 6564-6569, 2000). For example, a 18-bp spacer sequence containing the NotI site (5'-(G)-CGGCCG-CAGATCTTCACG-3'; SEQ ID NO: 3) is inserted into an adjacent gene locus of a cloned Sendai virus genomic cDNA (pSeV(+)) between the leader sequence and the 5'-terminus of a sequence encoding the N protein, and the plasmid pSeV18$^+$b(+) containing a self-cleavable ribozyme site derived from the antigenomic strand of the hepatitis delta virus is obtained (Hasan M. K. et al., J. General Virol., 1997, 78, 2813-2820). An exogenous gene fragment is inserted into the NotI site of pSeV18$^+$b(+) to obtain a recombinant Sendai virus cDNA into which a desired exogenous gene has been inserted.

The recombinant Paramyxovirus vector prepared as described above is transcribed in vitro or intracellularly, and RNP is reconstituted in the presence of viral L, P, and NP proteins to produce a viral vector comprising the RNP. The present invention provides a method for producing a Paramyxovirus vector encoding an angiogenic gene, the method comprising the steps of transcribing DNA encoding the Paramyxovirus vector genome intracellulary, in the presence of proteins that allow for transcription and replication of the genome, and recovering Paramyxovirus vector products. The proteins that allow for transcription and replication of Paramyxovirus vector genome include, for example, N, L, and P proteins. The present invention also provides DNA for producing a Paramyxovirus vector of the present invention, wherein said DNA comprises the above-mentioned DNA encoding the vector genome. The present invention also relates to the use of DNA encoding the vector genome, for producing Paramyxovirus vectors of the present invention. Reconstitution of a virus from virus vector DNA can be performed according to the known methods (WO 97/16539; WO 97/16538; Durbin A. P. et al., Virol., 1997, 235, 323-332; Whelan S. P. et al., Proc. Natl. Acad. Sci. USA, 1995, 92, 8388-8392; Schnell M. J. et al., EMBO J., 1994, 13, 4195-4203; Radecke F. et al., EMBO J., 1995, 14, 5773-5784; Lawson N. D. et al., Proc. Natl. Acad. Sci. USA, 1995, 92, 4477-4481; Garcin D. et al., EMBO J., 1995, 14, 6087-6094; Kato A. et al., Genes Cells, 1996, 1, 569-579; Baron M. D. and Barrett T., J. Virology, 1997, 71, 1265-1271; Bridgen A. and Elliott R. M., Proc. Natl. Acad. Sci. USA, 1996, 93, 15400-15404). These methods enable the reconstitution of desirable Paramyxovirus vectors including the parainfluenza virus, vesicular stomatitis virus, rabies virus, measles virus, rinderpest virus, and Sendai virus vectors from DNA. If the F, HN, and/or M genes are deleted from the virus vector DNA, infective virus particles will not be formed. However, it is possible to generate infective virus particles by introducing these deleted genes and/or genes encoding an envelope protein from another virus into the host cells and expressing them.

Methods for introducing vector DNA into cells may include (1) a method for forming DNA precipitates that can be incorporated into desired cells, (2) a method for making a complex that comprises positively charged DNA, that is suitable for being incorporated into desired cells and that has low cytotoxicity, and (3) a method for instantaneously opening a pore large enough for DNA to pass through in the desired plasma membrane using an electrical pulse.

A variety of transfection reagents can be used in (2), for instance, including DOTMA (Boehringer), Superfect (QIAGEN #301305), DOTAP, DOPE, and DOSPER (Boehringer #1811169). For (1), transfection using calcium phosphate can be used. In this method, DNA incorporated by cells is taken up into phagocytic vesicles, but it is known that a sufficient amount of DNA is also taken up into the nucleus (Graham F. L. and van Der Eb J., Virology, 1973, 52, 456; Wigler M. and Silverstein S., Cell, 1977, 11, 223). Chen and Okayama studied the optimization of the transfer technology and reported (1) that maximal efficiency is obtained when cells and precipitates are incubated under 2% to 4% $CO_2$ at 35° C. for 15 hr to 24 hr, (2) that circular DNA has higher activity than linear DNA, and (3) that the optimal precipitates are formed when the DNA concentration in the mixed solution is 20 µg/ml to 30 µg/ml (Chen C. and Okayama H., Mol. Cell. Biol., 1987, 7, 2745). The method of (2) is suitable for transient transfection. More classically, a transfection method in which DEAE-dextran (Sigma #D-9885 M. W. 5×10$^5$) is mixed with DNA at a desired concentration ratio is known. Because most complexes are degraded in the endosome, chloroquine may be added to enhance the transfection efficiency (Calos M. P., Proc. Natl. Acad. Sci. USA, 1983, 80, 3015). The method of (3); called electroporation, may be more broadly applied than the methods of (1) and (2) because it can be used for any kind of cells. The transfection efficiency can be maximized by optimizing the duration of pulse currents, the form of pulse, the strength of the electrical field (gap between electrodes, and voltage), conductivity of buffer, DNA concentration, and cell density.

In the present invention, transfection reagents are suitably used because, among the above three methods, the method of (2) is easy to perform and enables the testing of a large number of samples using a large amount of cells. Preferable transfection reagents include, the Superfect Transfection Reagent (QIAGEN, Cat No. 301305) and the DOSPER Liposomal Transfection Reagent (Boehringer Mannheim, Cat No. 1811169), but are not limited thereto.

Specifically, the reconstitution from cDNA is performed as follows.

LLC-MK2, a cell line derived from a monkey kidney, is cultured in a 24-well to 6-well plastic plate or in a 100-mm petri dish in minimum essential medium (MEM) containing 10% fetal calf serum (FCS) and an antibiotic (100 units/ml penicillin G and 100 µg/ml streptomycin) to be 70% to 80% confluent. Cells are then infected, for instance, at 2 pfu/cell with recombinant vaccinia virus vTF7-3 that expresses T7 polymerase, which has been inactivated by a 20-minute UV exposure in the presence of 1 µg/ml psoralen (Fuerst T. R. et al., Proc. Natl. Acad. Sci. USA, 1986, 83, 8122-8126; and Kato. A. et al., Genes Cells, 1996, 1, 569-579). The amount of psoralen and the duration of UV exposure can be optimized. One hour after infection, cells are transfected by, for example, lipofection using Superfect (QIAGEN) with 2 µg to 60 µg of, or more preferably 3 µg to 5 µg of the above recombinant Sendai virus cDNA together with expression plasmids for virus proteins (24-0.5 µg pGEM-N, 12-0.25 µg pGEM-P, and 24-0.5 µg pGEM-L, or more preferably 1 µg pGEM-N, 0.5 µg pGEM-P, and 1 µg pGEM-L) (Kato. A. et al., Genes Cells, 1996, 1, 569-579) that function in trans and are required for producing a full-length Sendai virus genome. The transfected cells are cultured in serum-free MEM containing, if desired, 100 µg/ml rifampicin (Sigma) and cytosine arabinoside (AraC) (Sigma), more preferably 40 µg/ml arabinoside alone, so that the drug concentration is adjusted to be optimal to minimize the cytotoxicity of the vaccinia virus and maximize the recovery of virus (Kato. A. et al., Genes Cells, 1996, 1, 569-579). Cells are cultured for 48 hr to 72 hr after transfection, then collected and lysed through three cycles of freeze-thawing. The cell lysates are transfected into LLC-MK2 cells, and after a 3-day to 7-day culture, the culture medium is collected. To reconstitute a virus vector lacking a gene encoding an envelope protein that is incapable of replication, the vector may be transfected into LLC-MK2 cells expressing an envelope protein, or co-transfected with expression plasmid for the envelope protein. Alternatively, transfected cells can be overlaid and cultured on LLC-MK2 cells expressing envelope protein to propagate a deletion virus vector (see International Publication Numbers WO 00/700.55 and WO 00/70070). The virus titer of the culture medium can be determined by measuring hemagglutinin activity (HA). The HA may be determined by "endo-point dilution" (Kato. A. et al., Genes Cells, 1996, 1, 569-579; Yonemitsu Y. and Kaneda Y., Hemagglutinating virus of Japan-liposome-mediated gene delivery to vascular cells., Molecular Biology of Vascular Diseases. Methods in Molecular Medicine, Ed. by Baker A. H., Humana Press, 1999, 295-306). To eliminate the possible contamination of vaccinia virus vTF7-3, the obtained allantoic fluid sample may be diluted appropriately ($10^6$ times for instance) and re-amplified in chicken eggs. Re-amplification may be repeated, for example, three times or more. The obtained virus stock can be stored at −80° C.

Host cells for viral reconstitution are not limited to any special types of cells as long as the virus vector can be reconstituted in the cells. Host cells may include monkey kidney-derived cells such as LLC-MK2 cells and CV-1 cells, cultured cell lines such as BHK cells derived from a hamster kidney, and human-derived cells. Furthermore, to obtain a large quantity of the Sendai virus vector, embryonated chicken eggs may be infected with virus vectors obtained from the above host cells and the vectors can be amplified. The method of producing virus vectors using chicken eggs has been established (Advanced protocols in neuroscience study III, Molecular physiology in neuroscience., Ed. by Nakanishi et al., Kouseisha, Osaka, 1993, 153-172). Specifically, for example, fertilized eggs are incubated for 9 days to 12 days at 37° C. to 38° C. in an incubator to grow the embryos. Virus vectors are inoculated into the allantoic cavity, and eggs are further incubated for several days to propagate the vectors. Conditions such as the duration of incubation may vary depending on the type of recombinant Sendai virus used. Then, the allantoic fluids containing viruses are recovered. Sendai virus vector is separated and purified from the allantoic fluid sample according to the standard method (Tashiro M., Protocols in virus experiments., Ed. by Nagai and Ishihama, MEDICAL VIEW, 1995, 68-73). Moreover, trypsin resistant cells (for example, cells such as LLC-MK2) are preferred for the mass production of F gene-deficient Sendai virus.

The construction and the preparation of Sendai virus vectors deficient in F gene can be performed, for example, as follows (see WO00/70055 and WO00/70070).

1. Construction of cDNA Encoding F Gene-Deficient Sendai Virus Genome for Cloning Endogenous Genes.

Full-length Sendai virus (SeV) genomic cDNA, pSeV18$^+$ b(+) (Hasan, M. K. et al., J. Gen. Virol. 78, 2813-2820, 1997) ("pSeV18$^+$b(+)" is also referred to as "pSeV18$^+$"), is digested with SphI/KpnI and the digested fragment (14673 bp) is recovered. The fragment is subcloned into pUC18 to obtain the plasmid pUC18/KS. Construction of F gene-deficient region is performed using pUC18/KS with a combination of PCR and ligation techniques. F gene-deficient SeV genomic cDNA (pSeV18$^+$/ΔF) is constructed by removing the F gene ORF (ATG–TGA=1698 bp) and filling in the gap with atg-catgccggcagatga (SEQ ID NO: 4). In PCR, primer pairs consisting of forward: 5'-gttgagtactgcaagagc (SEQ ID NO: 5) and reverse: 5'-tttgccggcatgcatgtttcccaagggagagttttgcaacc (SEQ ID No: 6) are used in the upstream of F gene, and primer pairs consisting of forward: 5'-atgcatgccggcagatga (SEQ ID NO: 7) and reverse: 5'-tgggtgaatgagagaatcagc (SEQ ID NO: 8) are used in the downstream of F gene. The PCR products are then ligated to the EcoT22I site. The thus-obtained plasmid is digested with SacI and SalI and the fragment (4931 bp) which contains the F gene-deficient region is subcloned into pUC18 to give pUC18/dFSS. This pUC18/dFSS is digested with DraIII and the digested fragment is recovered. The fragment is replaced with a F gene-containing DraIII fragment of pSeV18' to construct plasmid pSeV18$^4$/ΔF.

The EIS sequence (SeV specific sequence, E, end; I, intergenic; S, start) of the F gene remains in the construct and the construct may express polypeptides consisting of 5 amino acids derived from the primer used to connect the gap even though the downstream ORF of the F gene is removed.

The insertion of exogenous genes into the F gene-deficient region can be achieved using NsiI and NgoMIV restriction enzyme sites that are located at the F gene-deficient region in pUC18/dFSS. In order to clone exogenous genes into the region, for example, exogenous gene fragments can be amplified using an NsiI-tailed primer and an NgoMIV-tailed primer.

For example, EGFP gene is amplified first by PCR to construct a cDNA containing the EGFP gene (pSeV18$^+$/ΔF-GFP). In order to adjust the number of nucleotides of the EGFP gene fragment to contain a multiple of 6 (Hausmann, S. et al., RNA 2, 1033-1045, 1996), PCR is performed using NsiI-tailed primer (5'-atgcatatggtgatgcggttttggcagtac/SEQ ID NO: 9) as the 5' end primer and NgoMIV-tailed primer (5'-tgccggctattattacttgtacagctcgtc/SEQ ID NO: 10) as the 3' end primer. The PCR product is digested with restriction enzymes NsiI and NgoMIV and the fragment is recovered from a gel. The fragment is subcloned into the F gene-deficient region in pUC18/dFSS using NsiI and NgoMIV restriction enzyme sites and the sequence is confirmed. The DraIII fragment containing the EGFP gene is then recovered, replaced with the F gene-containing DraIII fragment of pSeV18$^+$, and ligated to obtain pSeV18$^+$/ΔF-GFP.

The insertion of exogenous genes into the upstream of the NP gene is achieved using the restriction enzyme NotI recognition site located in pSeV18$^+$/ΔF or pSeV18$^+$/ΔF-GFP. However, pSeV18$^+$/ΔF has a sequence that may express a 5-amino acid peptide derived from the primer used to connect to the F gene-deficient region. Moreover, GFP is co-expressed by pSeV18$^+$/ΔF-GFP. Therefore, the gene constructs are prepared as follows so that the peptides or GFP are not expressed, if it is necessary.

The fragment (6288 bp) which contains the F gene-deficient region is recovered by digesting pSeV18$^+$/ΔF-GFP with SalI and NheI and subcloned into Litmus 38 (New England Biolabs, Beverly, Mass.) to obtain LitmusSalINheIfrg/ΔF-GFP. Deletion of the EGFP gene containing the EIS sequence upstream of the F gene, which has been deleted, is conducted by the inverse PCR method. PCR is performed using a reverse primer (5'-gtttaccaggtggagagttttgcaaccaagcac/SEQ ID NO: 11) which is designed to contain the restriction enzyme SexAI recognition sequence upstream of the GFP gene and a forward primer (5'-ctttcacctggtacaagcacagatcatggatgg/SEQ ID NO: 12) which is designed to contain the restriction enzyme SexAI recognition sequence downstream of the GFP gene. The preferable sized fragment (10855 bp) is excised and ligated to delete the EGFP gene containing the EIS sequence upstream of the F gene, which has been deleted.

The resulting construct has an extra 15-bp sequence between the two SexAI sites due to the primer design. Therefore, the plasmid is used to transform E. coli SCS110 strain (dcm⁻/dam⁻ SCS110 strain is used because SexAI is methylated and cannot be digested with it). The plasmid is digested with restriction enzyme SexAI and two gene fragments, 1628 bp and 9219 bp, are recovered and ligated to remove the extra 15-bp fragment contained in LitmusSalINheIfrg/ΔF (Δ5aa), in which the EGFP gene containing the EIS sequence upstream of the F gene and having the multiple of 6 numbers of nucleotides is deleted. The plasmid is digested with SalI and NheI and the fragment is recovered, replaced with SalI/NheI fragment, which contains the F gene from pSeV18⁺, and ligated to obtain plasmid pSeV18⁺/ΔF (Δ5aa).

Insertion of an exogenous gene into the plasmid is performed, for example, using the recognition sequence of restriction enzyme NotI located upstream of the NP gene.

2. Construction of cDNA Encoding F Gene-Deficient Sendai Virus Genome Containing hFGF2 Gene Various methods are known for obtaining human FGF2 (hFGF2) cDNA. For example, RT-PCR is performed to isolate cDNA using vascular smooth muscle cells obtained from the human great saphenous vein with a patient's consent. The hGFG2 cDNA is then prepared by subcloning the amplified product into pBluescriptSK+ (Stratagene, La Jolla, Calif.) at HindIII (5' end) and EcoRI (3' end). The hFGF2 cDNA sequence can be confirmed by comparing with that in the report by Abraham et al. (Abraham, J. A. et al., EMBO J. 5 (10), 2523-2528, 1986). In order to insert the hFGF2 gene at the restriction enzyme NotI site located upstream of the NP gene, the hFGF2 gene fragment can contain the SeV specific sequence (EIS sequence) at its 3' end, and NotI recognition sequences at its both ends. Specifically, PCR is performed using the hFGF2 cDNA as a template and N-terminus primer (5'-atccgcggccgccaaagttcacttatg-gcagccgggagcatcaccacgctgc-ccgccttgcccgaggatggcggcagcggcgcc/SEQ ID NO: 13) containing a start codon and C-terminus primer (5'-atccgcggccgcgatgaactttcaccctaagttttcttactacggtcagctcttagca gacattggaagaaaaagtatagc/SEQ ID NO: 14) containing a stop codon region and the EIS sequence. The amplified fragment is digested with NotI and then subcloned into pBluescriptSK+ (Stratagene, La Jolla, Calif.) to obtain pBS-hFGF2. The nucleotide sequence is confirmed and, in case the gene contains mutations, mutations are corrected using, for example, QuickChange™ Site-directed Mutagenesis Kit (Stratagene, La Jolla, Calif.) according to the attached protocol. The fragment containing hFGF2 cDNA is obtained by digesting pBS-hFGF2 with NotI and inserted into pSeV18⁺/ΔF (Δ5aa) at the NotI site located upstream of the NP gene to construct F gene-deficient Sendai virus genomic cDNA containing hFGF2 gene, pSeV18⁺ hFGF2/ΔF (Δ5aa). Hereafter, pSeV18⁺hFGF2/ΔF (Δ5aa) is also indicated as pSeV18⁺ hFGF2/ΔF.

3. Construction of F Expression Plasmid

Plasmid pCALNdLw (Cre/loxP inducible expression plasmid; Arai, T. et al., J. Virol. 72 (2), 1115-1121, 1998), which is designed to induce the expression of gene products by Cre DNA recombinase, can be used to express the Sendai virus F gene (SeV-F). The fragment (1783 bp) containing the SeV-F gene is isolated by digesting pUC18/KS with StyI and BstUI, blunt ended, and inserted into pCALNdLw at a unique SwaI site to construct the F expression plasmid pCALNdLw/F.

4. Preparation of Helper Cell Line, which Inducibly Expresses SeV-F Protein

A helper cell line, which expresses SeV-F protein, is established to recover infectious virus particles from the F gene-deficient genome. For example, cells can be obtained from LLC-MK2 cells, monkey kidney-derived cell line, which is often used for SeV propagation. LLC-MK2 cells are cultured in MEM containing 10% heat inactivated fetal bovine serum (FBS), 50 U/ml Sodium Penicillin G and 50 µg/ml Streptomycin in an atmosphere containing 5% $CO_2$ at 37° C. The plasmid, pCALNdLw/F, which is designed to induce the expression of the F gene product by Cre DNA recombinase, is transferred into LLC-MK2 cells using the Calcium Phosphate method with Mammalian Transfection Kit (Stratagene, La Jolla, Calif.) according to protocols known to those skilled in the art.

Specifically, 10 µg of plasmid pCALNdLw/F is transferred into LLC-MK2 cells which are propagated to 40% confluence in a 10-cm dish and then the cells are cultured in 10 ml MEM medium containing 10% FBS in an incubator with an atmosphere of 5% $CO_2$ at 37° C. for 24 hours. Cells are scraped from the dish after 24 hours, suspended in 10 ml medium, and aliquoted to five 10-ml dishes so that, for example, 1 dish contains 5 ml, 2 dishes contain 2 ml, and 2 dishes contain 0.2 ml of cell suspension. Each cell is cultured in 10 ml MEM medium containing 1,200 µg/ml G418 (Gibco-BRL, Rockville, Md.) and 10% FBS for 14 days with a medium change every 2 days and stably-transfected cell lines are selected. For example, 30 strains of G418 resistant cells, grown in the medium, are recovered using a cloning ring. Each clone is propagated until it becomes confluent in a 10-cm dish.

Selection of stably-transfected cell lines with F gene is carried out as follows. Specifically, the expression level of F protein can be analyzed semi-quantitatively by Western blotting. The cells are cultured to confluence in 6-cm dishes and then infected with Adenovirus AxCANCre at moi=3 by the method by Saito et al. (Saito et al., Nucl. Acids Res. 23, 3816-3821, 1995; Arai, T. et al., J. Virol. 72 (2), 1115-1121, 1998) to induce expression of F protein in each clone. Three days after infection, the culture medium was removed from the dish, and then cells were washed twice with PBS buffer, scraped with a scraper, centrifuged at 1500×g for 5 min, and collected. The cells are stored at −80° C. and resuspended in 150 µl PBS buffer after thawing. An equal amount of 2× Tris-SDS-BME sample loading buffer (0.625 M Tris (pH 6.8), 5% SDS, 25% 2-ME, 50% glycerol, and 0.025% BPB, Owl Separation Systems) is added thereto. The mixture is heat-treated at 98° C. far 3 min and then subjected to electrophoresis. The samples (1×10⁵ cells per lane) are then subjected to SDS-polyacrylamide gel electrophoresis followed by Western blotting according to known protocols. SeV-F expression level is semi-quantitatively measured by Western blotting using 1:1000 dilution of anti-SeV-F antibody (f236) as the primary antibody.

By the method as described above, the establishment of LLC-MK2 cells in which SeV-F gene product can be inducibly expressed, is confirmed. Hereafter, these cells before the induction of SeV-F gene expression are described as LLC-MK2/F and the cells after the induction are described as LLC-MK2/F/Ad.

5. Reconstitution and Amplification of F Gene-Deficient Sev

F gene-deficient Sendai virus genomic cDNA containing angiogenic gene (s) can be reconstituted by transfecting helper cells expressing F gene with it. For example, F gene-deficient Sendai virus genomic cDNA containing the hFGF2 gene (pSeV18⁺hFGF2/ΔF) as described above is used to transfect LLC-MK2 cells as follows. LLC-MK2 cells are seeded onto 10-cm petri dishes at a density of 5×10⁶ cells/dish, incubated for 24 hours, and transfected (at moi=2 to 3, preferably 2) for 1 hour at room temperature with recombinant Vaccinia virus expressing T7 RNA polymerase (Fuerst, T. R. et al., Proc. Natl. Acad. Sci. USA 83, 8122-8126, 1986) which has been treated with long wave UV (365 nm) and Solaren for 20 min. For UV exposure of the Vaccinia virus, for example, UV Stratalinker 2400 (Catalog No. 400676 (100V), Stratagene, La Jolla, Calif., USA) which is equipped with five 15-watt bulbs is used. Cells are washed twice and the plasmids pSeV18+hFGF2/ΔF, pGEM/NP, pGEM/P, pGEM/L (Kato, A., et al., Genes Cells 1, 569-579, 1996), and pGEM/F—HN (WO 00/70070) are resuspended in OptiMEM (GIBCO) at ratios of 12 μg, 4 μg, 2 μg, 4 μg, and 4 μg/dish, respectively, and mixed with SuperFect transfection reagent (1 μg DNA/5 μl of Superfect, QIAGEN). Mixtures are left standing at room temperature for 15 min and then added to 3 ml OptiMEM containing 3% FBS. The resulting mixture is added to the cells and incubated for 3 to 5 hours. Cells are then washed twice with serum-free MEM and incubated in serum-free MEM containing 40 μg/ml of cytosine β-D-Arabinofuranoside (AraC, Sigma) and 7.5 μg/ml trypsin (GIBCO) for 24 hours.

The culture medium is removed from the cell culture and helper cell expressing F gene, LLC-MK2/F/Ad cells, which have been constructed as described above, are layered on the cells. Specifically, LLC-MK2/F/Ad cells are resuspended in serum-free MEM (containing 40 μg/ml AraC and 7.5 μg/ml trypsin), layered on the cells without culture medium, and then incubated for 48 hours. Cells are collected using a scraper and pellets are resuspended in OptiMEM ($10^7$ cells/ml) and freeze-thawed three times. The lysates are added (200 μl/well) to the LLC-MK2/F/Ad cells ($4 \times 10^6$ cells/well in 12-well-plate) and additional 300 μl/well of serum-free MEM (containing 40 μg/ml AraC, 7.5 μg/ml trypsin) is added to each well and then incubated for 15 hours to 24 hours. The culture medium is removed, and cells are washed with serum-free MEM, and replaced with fresh serum-free MEM (containing 40 μg/ml AraC and 7.5 μg/ml trypsin). Cells are incubated for 5 days to 9 days and the culture medium is collected. The collected medium contains reconstituted F gene-deficient SeV particles. The F gene-deficient SeV particles can be amplified by infecting into LLC-MK2/F/Ad cells and culturing (or repeating the process) the cells in serum-free MEM (containing 40 μg/ml AraC and 7.5 μg/ml trypsin).

At this time, contamination of the recombinant Vaccinia virus which is used to express. T7 RNA polymerase during reconstitution, is mostly prevented by filtering the culture medium containing F gene-deficient SeV particles twice with a 0.22 μm filter. Specifically, the culture (post-P2 samples) amplified twice or more in serum-free MEM containing AraC (containing 40 μg/ml AraC and 7.5 μg/ml trypsin) are filtered twice with 0.22 μm filter and the culture is further amplified once in serum-free MEM containing AraC (containing 40 μg/ml AraC and 7.5 μg/ml trypsin) to obtain amplified F gene-deficient SeV which can serve as SeV free from recombinant Vaccinia virus contamination.

In preparing deletion virus vectors, two different virus vectors having deletion of a different envelope gene in the genome may be transfected into the same cell. In this case, each deleted envelope protein is supplied through expression from the other vector, and this mutual complementation permits the generation of infective virus particles, which can replicate and propagate. Thus, two or more of the virus vectors of the present invention may be simultaneously inoculated in a combination that complement each other, thereby producing a mixture of each envelope deletion virus vector at a low cost and in a large scale. Because these viruses lacking an envelope gene have a smaller genome, they can allow the insertion of a long exogenous gene. In addition, it is difficult for these viruses, which are intrinsically non-infective, to keep the status of co-infection after being diluted outside cells, and thus they are sterilized and less harmful to the environment.

Once a viral vector is prepared using, as the exogenous gene, a gene for the treatment of a disease, then the vector can be administered to perform gene therapy. When the viral vector of the present invention is used in gene therapy, an exogenous gene that ensures desired therapeutic effects or an endogenous gene whose expression is impaired in the body of a patient can be expressed either by a method of direct administration or by a method of indirect (ex vivo) administration for gene expression. There is no limitation on the type of exogenous gene as long as it is an angiogenic gene or promotes angiogenesis, including not only a nucleic acid encoding a protein but also a nucleic acid encoding no protein, for example, ribozyme or antisense nucleic acid of a gene suppressing angiogenesis.

The collected Paramyxovirus can be purified to be substantially pure. Purification can be carried out by a known purification/separation method such as filtration, centrifugation, and column purification, or the combination thereof. The term "substantially pure" means that a virus comprises the major portion in a sample where it is present as a component. Typically, a substantially pure virus vector in a sample can be confirmed when protein derived from the virus vector occupies 50% or more, preferably 70% or more, more preferably 80% or more, yet more preferably 90% or more, of the total proteins in the sample. Exemplary purification methods specific for Paramyxovirus include methods using cellulose sulfuric ester or cross-linked polysaccharide sulfuric ester (Examined Published Japanese Patent Application No. (JP-B) Sho 62-30752; JP-B Sho 62-33879; and JP-B Sho 62-30753), and methods which comprise allowing polysaccharide comprising fucose sulphuric acid and/or its degradation product (WO 97/32010).

The Paramyxovirus vector of the present invention can be made as a composition together with a desired, pharmaceutically acceptable carrier or medium. A "pharmaceutically acceptable carrier," as defined herein, refers to those materials that can be administered with a vector and do not significantly inhibit gene transfer achieved by the vector. For instance, the Paramyxovirus vector of the present invention may be appropriately diluted with a medium such as saline and phosphate buffered saline (PBS), to prepare a composition. If the Paramyxovirus vector of the invention is propagated in chicken eggs, the composition may contain allantoic fluids. In addition, the composition may contain media such as deionized water or a 5% dextrose aqueous solution. It may further contain stabilizers, antibiotics, and such. The present invention provides a method for producing angiogenic compositions in the present invention, which comprises the step of mixing the vector of the present invention with the pharmaceutically acceptable carriers. The present invention also relates to the usage of the vectors of the present invention for producing the angiogenic compositions in the present invention. The compositions in the present invention are also useful as pharmaceutical compositions. The present invention relates to ischemia therapeutic formulations including the vectors in the present invention and pharmaceutically acceptable carriers. The present invention also relates to the use of the vectors and the compositions of the present invention as pharmaceuticals.

Angiogenic genes carried by Paramyxovirus vectors can be transferred by administering Paramyxovirus vectors constructed as described above or the compositions containing the vectors. The present invention provides the method for inducing angiogenesis which comprises the step of administering Paramyxovirus vectors of the present invention or angiogenic compositions of the present invention. The method is especially useful to treat ischemic tissues. Although there is no limitation to the sites of administration, local administration of the transgene directly into ischemic tissues or their surrounding areas is preferable so that expression products are concentrated in ischemic tissues and are prevented from leaking into the circulatory system. Alternatively, it is preferable to express the transgenelocally in the target tissue areas using proper gene delivery systems. For example, gene delivery can be achieved by administering Paramyxovirus vector-containing compositions of the present invention from inside or outside of ischemic tissues in vivo in order to express exogenous genes in the ischemic tissues. In addition, it may be achieved by ex vivo administration. For example, cells transfected with Paramyxovirus vectors encoding angiogenic genes can be injected into ischemic tissue areas or infused into arteries, which flow through the ischemic tissues.

Furthermore, local administration using a catheter can be selected. For example, vectors of the present invention can be administered by the double balloon catheter method, in which the vector compositions are infused into the area where the blood vessel is separated by two balloons, or by the administration method using a porous balloon (Jorgensen, B. et al., Lancet 1 (8647): 1106-8, 1989; Wolinsky, H. and Thung, S. N., J. Am. Coll. Cardiol. 15 (2): 475-81, 1990; WO 93/00051; WO 93/00052). Hydrogel-coated balloons can also be used as described above (Takeshita, S. et al., Lab. Invest. 75 (4): 487-501, 1996).

For example, the vector compositions of the present invention can be directly infused into myocardium through the ventrical cavity using a catheter to treat, for example, cardiac infarction, angina, or other ischemic cardiac diseases. Moreover, angiogenesis and development of collateral circulation in the area of stenosis in the coronary artery can be promoted by local infusion of the vectors of the present invention using a catheter.

However, the use of a catheter to administer the vectors requires a relatively long period of incubation and may cause vascular injury by the balloon. Moreover, it is often difficult to insert a catheter into diffuse blood vessels in ischemic tissues. Intramuscular (IM) administration of the vectors is especially preferred for the treatment of ischemic tissues in the present invention. Intramuscular administration is easier than administration using a catheter and the risk of damaging a blood vessel is low. The vectors of the present invention are administered into, for example, ischemic tissues or striated muscles surrounding the ischemic tissues. Striated muscles include skeletal and cardiac muscles. Bupivacaine, which is known to promote the expression of transgenes by inducing regeneration of muscles, can be administered before the administration of the virus vectors. Moreover, intradermal (ID) administration can also be selected. The vectors can be transferred into muscles, for example, subcutaneously or directly through a skin incision. It is necessary to be careful not to damage fascia during the vector transfer. For example, administration can be conducted using needles and syringes, or a bioinjector, which does not require the use of needles. Administration can be carried out either at a single place or multiple places. Moreover, administration can be carried out either once or multiple times.

The vectors of the present invention can be effectively administered in the form of a matrix. An exemplary method can be performed by dispersing virus vectors in aterocollagen matrix and solidifying the resulting mixture by freeze-drying, thereby allowing the matrix to gradually degrade. The use of this method has been reported to be useful for lasting effects of Adenovirus vectors known for their transient gene expression and of naked DNA (Ochida, T. et al., Nature Medicine 5, 707-710, 1999). The virus vectors of the present invention can be formulated with these auxiliary agents and can be freeze-dried. Moreover, a lipid cation can be added to increase the expression effect.

It is known that even a small administrative matrix can gradually release proteins such as growth factors over a long period of time through needles of approximate size of 18 gauge. For example, in the case of protein formulations are administered, the effectiveness of formulations such as a growth hormone last longer, for example, 7 days or more, than when formulations such as a growth hormone are administered alone. There is a report that the effectiveness can usually last 10 days or more (Unexamined Published Japanese Patent Application No. (JP-A) Hei 10-001440). This method thus enables to significantly reduce the number of administrations and amount of pain suffered by patients. The formulations can be used as, for example, solid injections (such as implants), which are administered subcutaneously and intramuscularly and mucous membrane absorbents such as suppositories. The shapes of the solid formulations for injection are often particle- or rod-shaped, which can be administered by injection needles. Particle shapes such as sphere shape, and rod shapes such as square and cylindrical shapes, are preferred shapes for formulation.

The size of the parenteral formulation of the present invention can be chosen depending on the type of administration and any size is suitable as long as it does not cause excess pain to patients. When the injection consists of a rod-shaped matrix of, for example, 3 mm or less (for example, 0.1 mm to 3 mm) in diameter and 30 mm or less (for example, 0.5 mm to 30 mm) in length, preferably 1.3 mm or less (for example, 0.1 mm to 1.2 mm) in diameter and 20 mm or less (for example, 0.5 mm to 20 mm) in length, which can be administered with an injection needle 14 gauge or smaller, and more preferably that of 0.1 mm to 1 mm in diameter and about 1 mm to 20 mm in length. The matrix is preferably cylindrical. Moreover, when the injection contains a particle-shaped matrix, the maximum diameter must be 1 mm or less (for example, about 0.1 µm to 1 mm), preferably, 150 µm or less (for example, about 0.5 µm to 100 µm), more preferably, about 1 µm to 100 µm. Moreover, the weight of the matrix can be chosen depending on the shape of the formulation and for injection, the weights are often 40 mg or less, preferably, 1 mg to 25 mg.

The genes transferred by the Paramyxovirus vector of the present invention are not limited as long as they promote angiogenesis and/or vascularization. For example, genes encoding aFGF, FGF2 (bFGF), VEGF, Ang (including Ang-1 and Ang-2), EGF, TGF-α, TGF-β, PD-ECGF, PDGF, TNF-α, HGF, IGF, EPO, CSF, M-CSF, GM-CSF, IL-8, and NOS, as described above, are used. These proteins include each member and isoform belonging to each family. One example especially suitable as an angiogenic gene, which is transferred by the Paramyxovirus vector of the present invention, is the gene encoding FGF2. FGF2 is, for example, anticipated to be applicable for acute ischemia therapy. For example, a significant therapeutic effect for acute critical ischemic limbs can be expected. Moreover, FGF2 shows a therapeutic effect for cardiac infarction (Yanagisawa-Miwa, A. et al., Science 257 (5075): 1401-3, 1992). Proteins can be a secretory protein, a membrane protein, a cytoplasmic protein, or a nuclear protein. Preferably, a secretory protein is used. Moreover, proteins may be artificially synthesized. Examples of artificially synthesized proteins are fusion proteins with other proteins, dominant negative proteins (including soluble molecules of receptors or membrane-binding dominant negative receptors), deficient forms of cell adhesion molecules, and cell surface molecules. Moreover, proteins attached to secretory signals, membrane localization signals, nuclear import signals, and such can be used. The transgenes can be endogenously induced to be expressed in ischemic tissues. It is also possible that their expressions are not induced but can be expressed at different sites. Moreover, the function of the undesired genes expressed in ischemic tissues can be suppressed by expression of antisense RNA molecules or RNA cleaving ribozymes.

The vectors of the present invention are expected to be applicable for gene therapy to treat various ischemic diseases as well as diseases that are treatable by angiogenesis. Such gene therapy includes, for example, the treatment for ischemia caused by vascular sever, infarction, and hemostatis due to vascular dissociation. The ischemic diseases treatable by the vectors of the present invention are, for example, cerebrovascular ischemia, kidney ischemia, lung ischemia, limb ischemia, ischemic cardiomyopathy, and myocardial ischemia. Tissues that are applicable for gene therapy are not specifically limited and, for example, muscles, brains, kidneys, and lungs can be used. Moreover, it is effective for promoting angiogenesis in transplants. Furthermore, it is useful for constructing various disease models and for developing or evaluating treatment methods in disease models.

Accelerated angiogenesis by vector administration can be confirmed by, for example, measuring the density and analyzing the number of capillary vessels in biopsy samples, and images by angiography. Moreover, it can also be confirmed by blood flow analysis using Doppler perfusion image analysis. The treatment effect on ischemic tissues is confirmed by macroscopic observation of tissue necrosis or tissue amputation or the microscopic observation of tissue samples.

Paramyxovirus vectors of the present invention are administered into target tissues at pharmaceutically effective doses and, thus, the vectors are transferred into the cells of the target tissues. "Pharmaceutically effective dose" means an amount of genes to be introduced into the cells of the target tissues, which achieves the preferable treatment effect or disease prevention effect at least partially. Angiogenic factors are produced from the cells, to which the vectors are transferred, by administering an effective dose of Paramyxovirus vectors of the present invention containing the desired angiogenic genes. Preferably, significant levels of angiogenic factors are detected in the tissues where the effective dose of the vectors of the present invention containing the desired angiogenic genes are administered. The phrase "significant level" indicates that the amount of expression (amount of transcription and translation products) of the genes transferred by the vectors of the present invention is detectable. For example, it indicates that the maximum expression level of the transferred gene is significantly enhanced as compared to the expression level of the endogenous gene when an endogenous gene corresponding to the transgene exists. Preferably, the expression level of the angiogenic genes at the site of administration is 1.2 times or more greater than the expression level of the endogenous gene, preferably 1.5 times or more, more preferably 2 times or more, even more preferably 10 times or more, and most preferably 20 times or more. However, the expression level of the transgene should be decided by considering the effective expression dose and toxic levels.

The expression level of the transgenes in the cells can be assayed by methods well known to those in the art. The transcriptional products of the genes can be detected and quantified by the methods such as, Northern hybridization, RT-PCR, and RNA protection assay. In situ detection can be performed by methods such as Northern hybridization and RT-PCR. Western blotting, Immuno precipitation, RIA, ELISA, Pull-down assays, and such, using antibodies, can be performed to detect translational products. Moreover, to make the detection of expression products of the transgene easier, tags can be attached to the expressed protein or reporter genes can be inserted such that the reporter genes are expressed. Examples of reporter genes include, without limitation, β-galactosidase, chloramphenicol acetyl transferase (CAT), alkaline phosphatase, and green fluorescence protein (GFP) genes.

A dose of the vector may vary depending on the disease, the body weight, age, sex, symptom, the purpose of administration, the transgene, and such, but it can be appropriately determined by those skilled in the art. The dose of the vector may be preferably within the range of about $10^5$ cell-infectious units (CIU)/ml to about $10^{11}$ CIU/ml, and more preferably about $10^7$ CIU/ml to about $10^9$ CIU/ml, but most preferably about $1 \times 10^8$ CIU/ml to about $5 \times 10^8$ CIU/ml, with pharmaceutically acceptable carriers. The composition of the present invention comprising the virus may be administered into subjects including all mammalian animals including humans, monkeys, mice, rats, rabbits, sheep, cattle, and dogs.

The dose for humans is preferably within the range of $2 \times 10^8$ CIU to $2 \times 10^{18}$ CIU in general for each administration site, more preferably, a dose of around $2 \times 10^9$ CIU, for example, within the range of $5 \times 10^8$ CIU to $1 \times 10^{10}$ CIU. The frequency of administration is once or more times within the range of clinically acceptable side effects. The frequency of the administration per day is the same. For non-human animals, for example, administration can be done by increasing or decreasing the number of administration sites or by calculating the doses based on the weight ratio of human to the target animals or the weight ratio or volume ratio of target sites (such as ischemic tissues).

The references cited throughout this description are incorporated herein by reference.

DETAILED DESCRIPTION OF THE INVENTION

Figure 1:
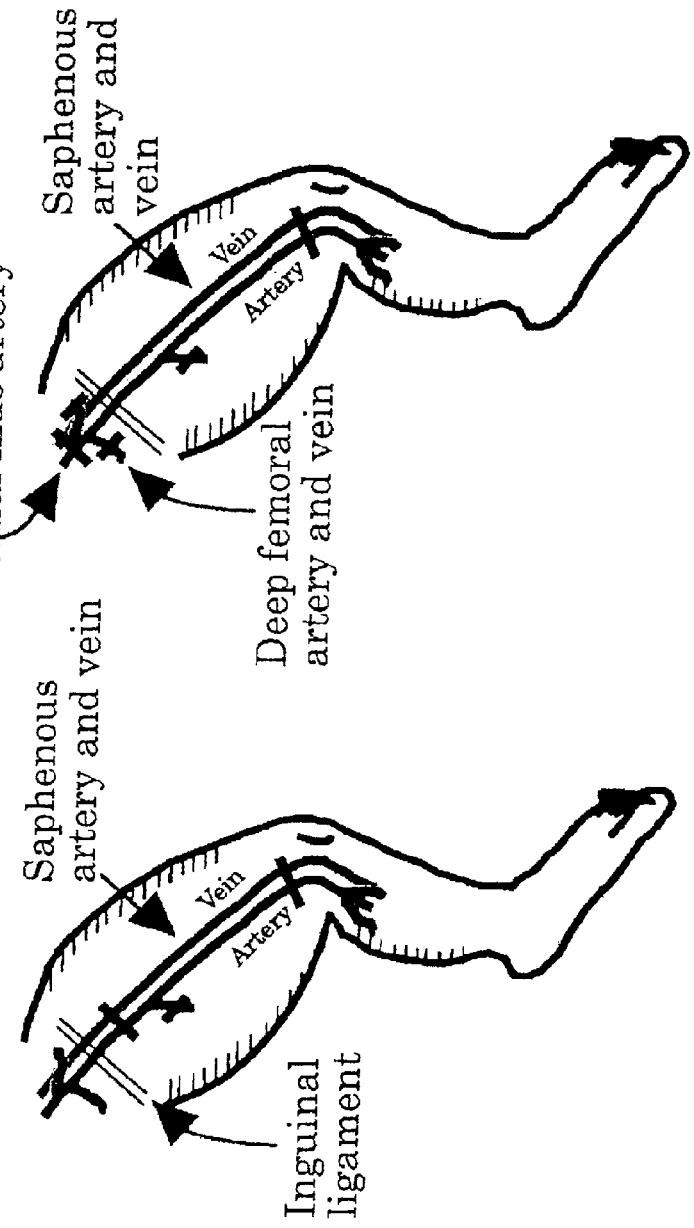
FIG. 1 is a schematic representation of operative procedures for moderate (left panel) and severe (right panel) acute hind limb ischemia of mice. Branched lines indicate arteries and veins in hind limb. Short thick lines indicate excisional sites of vessels.

The present invention is specifically illustrated below with reference to Examples, but it is not to be construed as being limited thereto.

Recombinant SeV was prepared as described previously (Yu, D. et al., Genes Cells 2(7): 457-66, 1997; Yonemitsu, Y., et al., Nature Biotech. 18, 970-973 (2000); Kato, A., et al., Genes Cells 1, 569-579 (1996); Hasan, M. K., et al., J. Gen. Virol. 78, 2813-2820 (1997)).

Virus titer was determined by hemagglutination assay using chicken red blood cells, and high titer stock ($10^9$ pfu/ml) was kept at −80° C. until use. Human VEGF165 cDNA was isolated by RT-PCR as described previously (Yonemitsu, Y., et al., Lab. Invest. 75, 313-323 (1996)). Full-length mouse FGF2 cDNA as described in Imamura, T., et al., Science 249, 1567-1570 (1990) was prepared by PCR. Specifically, the full-length cDNA was amplified using a partial mouse FGF2 cDNA fragment (a fragment of position 7 to 435 nucleotide of Accession Number M30644), which is missing the start and stop codon regions as a template, and N-terminus primer (5'-ACGTGCGGCCGCCAAAGTTCATCCAC-CATGGCTGCCAGCGGCATCACCTCGCTTCCC-3'/SEQ ID NO: 15) containing the start codon of mouse FGF2 cDNA and C-terminus primer (5'-ACGTGCGGCCGCGAT-GAACTTTCACCCTAAGTTTTTCTTAC-TACGCGGATCAGCTCTTAGCAGACATTG-GAAGAAACAGTATGGCCTTCTGTCCAGGTCCCGT-3'/ SEQ ID NO: 16) containing the stop codon and SeV specific sequence. The human VEGF165 and mouse FGF2 cDNAs, prepared as described above, were cloned into pSeV18$^+$b(+) (Hasan, M. K. et al., 1997, J. General Virology 78: 2813-2820) at a NotI site after each nucleotide sequence was confirmed. Sendai virus vectors, which express human VEGF165 or mouse FGF2, were referred to as SeV-VEGF165 or SeV-FGF2, respectively. SeV-luciferase (Hasan, M. K. et al., J. Gen. Virol. 78 (Pt 11): 2813-2820, 1997; Yonemitsu, Y. et al., Nature Biotechnol. 18: 970-973, 2000) and pCMV-luciferase (Yonemitsu, Y. et al., Nature Biotechnol. 18: 970-973, 2000) were prepared as described above.

All data of Examples of the present invention were represented as mean±S.D. in statistical analysis. The data except that of limb salvage were analyzed by one-way ANOVA with Scheffe's adjustment. For limb salvage, rate expressed by limb salvage score (LSS) was analyzed by Kaplen-Mayer's method. The statistical significance of the limb salvage experiments was determined using the log-rank test and $p<0.05$ was considered as significant in all statistical analyses.

The present invention provides the basic technology for gene therapy that targets ischemic tissues. Angiogenesis in the ischemic tissues can be effectively induced and necrosis can be prevented by using the gene transfer of the present invention.

Example 1

Ischemia-Induced Endogenous VEGF Expression does not Contribute to Local Protein Accumulation in Hind Limb Muscle To assess the therapeutic and adverse effects of angiogenic factors, the present inventors established following 3 models of limb ischemia by 2 different operations (FIG. 1): (1) moderate limb ischemia model of C57BL/6 mice in which whole femoral artery and vein, and saphenous arteries and vein have been excised (FIG. 1 left panel) (Couffinhal, T., et al., Am. J. Pathol. 152, 1667-1679 (1998); Kalka, C., et al., Proc. Natl. Acad. Sci. USA 97, 3422-3427 (2000)); (2) severe ischemia model of C57BL/6 mice in which whole external iliac artery and vein, femoral artery and vein, and all related branches have been excised (FIG. 1 right panel); and (3) immune deficient BALB/c nu/nu mice subjected to same surgical procedures as (2) (i.e., severe ischemia model of BALB/c nu/nu mice).

Adult male C57BL/6, BALE/c, and BALB/c nu/nu mice (6-8 weeks old, Charles River Grade) were purchased from KBT Oriental Co. Ltd. (Tosu, Saga, Japan). Animal experiments were performed using approved protocols and in accordance with recommendations for the proper care and use of laboratory animals by the Committee for Animals', Recombinant DNA, and Infectious Pathogens' Experiments at Kyushu University and were done according to the law (No. 105) and Notification (No. 6) of the Japanese Government and "Principles of Laboratory Animal Care" and "Guide for the Care and Use of Laboratory Animals" by National Institute of Health of USA (publication No. NIH 80-23, revised 1985).

Under sufficient anesthesia using intraperitoneal injection of pentobarbital; mice were subjected to skin incision. For the moderate ischemia model, whole superficial femoral artery and vein and saphenous artery and vein (from just below of deep femoral arteries to popliteal artery and vein) was ligated, cut, and removed (FIG. 1, left panel) (Couffinhal, T., et al., Am. J. Pathol. 152, 1667-1679 (1998); Kalka, C., et al., Proc. Natl. Acad. Sci. USA 97, 3422-3427 (2000)). For the severe ischemia model, additional excision of external iliac artery and vein with deep femoral artery were also made (FIG. 1, right panel). Reproducibility of limb prognosis of these models were confirmed by the 3 to 5 separate experiments using 10 or more animals/model by same operator (I. M.). Each limb salvage experiments contained animals subjected to 4 individually separate experiments.

The model (1) as described above never lost their limbs, occasionally showing only a sign of toe necrosis. Further, the model (2) (severe ischemia model of C57BL/6 mice) did not show limb necrosis (called "limb salvage model") and all animals of the model (3) (severe ischemia model of BALB/c nu/nu mice) resulted in nearly total limb amputation within 10 days after operation (called "auto-amputation model"). The severe ischemia model of immunocompetent BALB/c mice also showed similar degree of limb necrosis to BALB/c nu/nu mice (data not shown). Together with a previous report indicating that BALB/c mice are more susceptible to angiogenesis against growth factors than C57BL/6 mice (Rohan, M. R. et al., FASEB J. 14, 871-876 (2000)), these results suggests that limb salvage in C57BL/6 mice seems to be depend rather on better collateral limb circulation than on susceptibility to angiogenesis.

The present inventors assessed the endogenous expression of VEGF and FGF2 in the ischemic muscle and serum of the moderate and severe ischemia model as described above. Two days after operation, each limb muscle (whole thigh and calf muscle) and serum of C57BL/6 mice were collected, and their tissues are homogenized or lysated, and then subjected to enzyme-linked immunosorbent assay (ELISA). Recombinant proteins were synthesized using Quantikine Immunoassay systems (R & D Systems Inc., Minneapolis, Minn.) for human VEGF or mouse FGF2, and then quantified according to its instruction. The concentrations of total proteins were determined by Bradford method using protein assay system (Bio-Rad Laboratories, Hertfordshire, UK) and standardized (Yonemitsu, Y., et al., Nature Biotech. 18, 970-973 (2000))

Figure 2:
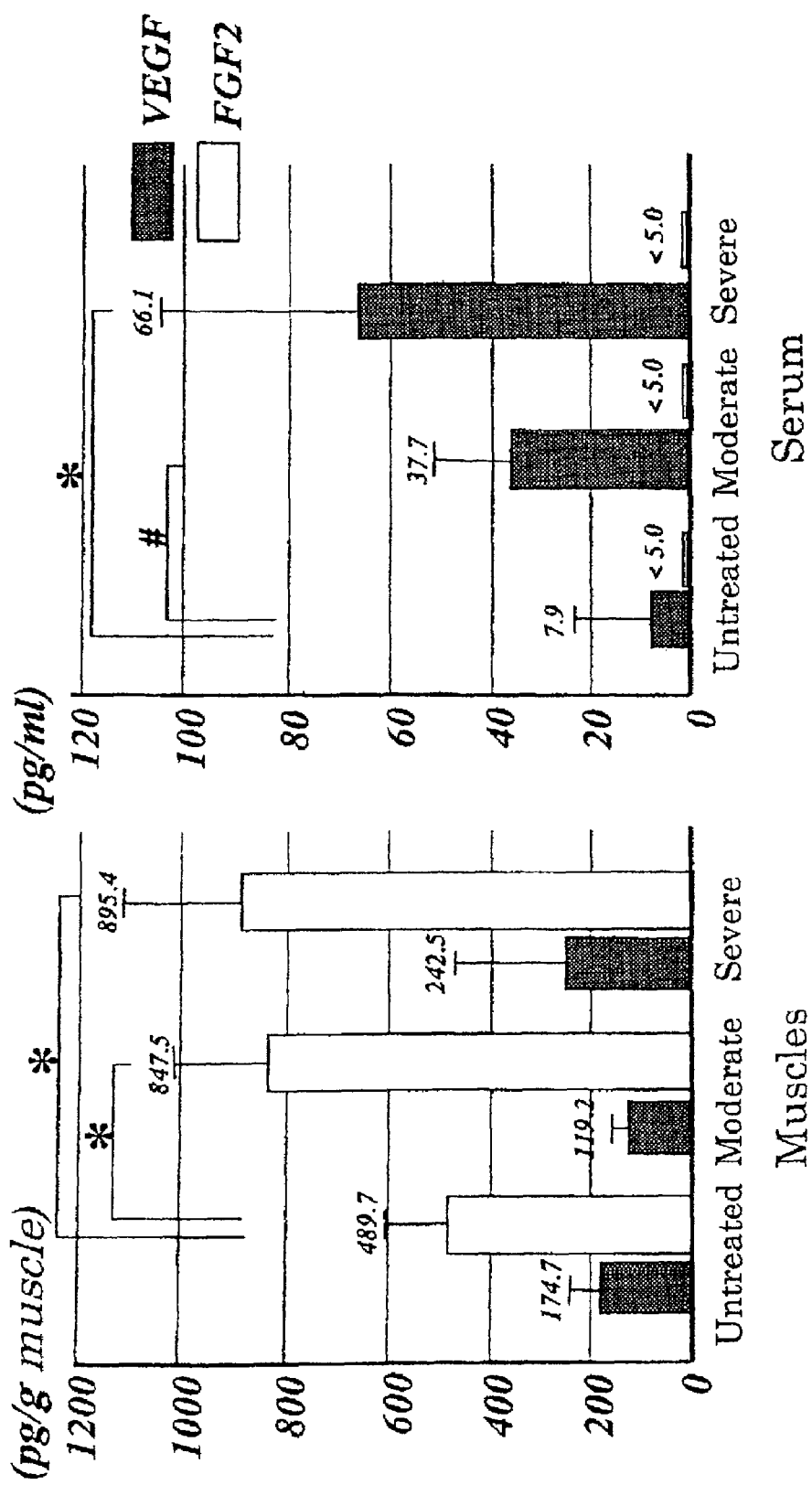
FIG. 2 is graphs showing hind limb ischemia-related expression of endogenous VEGF (solid) and FGF2 (hollow) in muscle (left graph) and serum (right graph). Moderate and severe ischemia models of C57BL/6 mice were used. Two days after operation, all thigh and calf muscles (n=6) and serum (n=6) were obtained, and subjected to enzyme-linked immunosorbent assays (ELISA). Values were standardized by total extracted protein of muscle or volume, respectively, and expressed with mean±S.D. Values of muscle contains both data of thigh and calf (i.e., n=12 in each group). Mean values are shown in the graph. *$P<0.01$, #$P<0.05$ (analyzed by one-way ANOVA).

Since there were no significant differences in protein concentration between thigh and calf muscles, both were included in each group. Interestingly, ischemic operation significantly enhanced FGF2 protein content in both hind limb ischemia model mice (the moderate model, 847.5±187.7 pg/g muscle; the severe model, 895.4±209.5 pg/g muscle; each n=12), compared to baseline (489.7±108.6 pg/g muscle; n=12) for untreated mice (P<0.001) (FIG. 2). On the other hand, ischemia-related enhancement of VEGF expression was seen in the severe ischemic group, but not significant in the muscles (Untreated, 174.7±43.1; Moderate, 119.2±53.4; and Severe, 242.5±244.3, n=12). These seemed paradoxical results because VEGF is a well-known mitogen strongly induced by tissue ischemia (Shweiki, D. et al., Nature 359, 843-845 (1992); Forsythe, J. A., et al., Mol. Cell. Biol. 16, 4604-4613 (1996)). The present inventors measured VEGF level in serum since VEGF may leaked to systemic circulation. As expected, severity-dependent increase of VEGF protein level in serum was observed, while FGF2 level in serum could not be detected (FIG. 2, right panel).

The present inventors hypothesized that limb ischemia may induce rather smaller isoforms of VEGF which is well-known less to interact to heparin sulfate than medium- or larger-sized VEGF (Cohen, T., et al., J. Biol. Chem. 270, 11322-11326 (1995)). To assess this hypothesis, the present inventors analyzed expression of VEGF isoforms in thigh muscle of C57BL/6 male mice a day after operation. The analysis was performed by RT-PCR using primer sets which can differentiate murine VEGF splicing isoforms including VEGF188, 164, 144, and 120 (Burchardt, M., et al., Biol. Reproduct. 60, 398-404 (1999)). Primer sets were previously reported (Burchardt, M., et al., Biol. Reproduct. 60, 398-404 (1999)) for rat VEGF on exon 1 and exon 8: forward primer (5'-TGC ACC CAC GAC AGA AGG GGA-3'/SEQ ID NO: 17) and reverse primer (5'-TCA CCG CCT TGG CTT GTC ACA T-3'/SEQ ID NO: 18), which correspond to sequences of murine VEGF isoforms. For detecting smallest isoform of murine VEGF (VEGF115), same forward primer as above and VEGF115-specific reverse primer (5'-CTA CCA AAA GTT TCC CAG GCA G-3'/SEQ ID NO: 19) were used (Sugihara, T. et al., J. Biol. Chem. 273, 3033-3038 (1998)). RT-PCR was performed under conditions according to literatures (Burchardt, M., et al., Biol. Reproduct. 60, 398-404 (1999); Sugihara, T. et al., J. Biol. Chem. 273, 3033-3038 (1998)).

Figure 3:
FIG. 3 is a photograph showing the result of RT-PCR for detecting induction of VEGF expression due to ischemia.

As a result, ischemia-related endogenous VEGF expression was seen only in 164 isoform, while no apparent other isoforms' expression was detected (FIG. 3). Additional RT-PCR analysis cannot detect the expression of a known smallest isoform, VEGF115 (Sugihara, T. et al., J. Biol. Chem. 273, 3033-3038 (1998)).

Example 2

Figure 4:
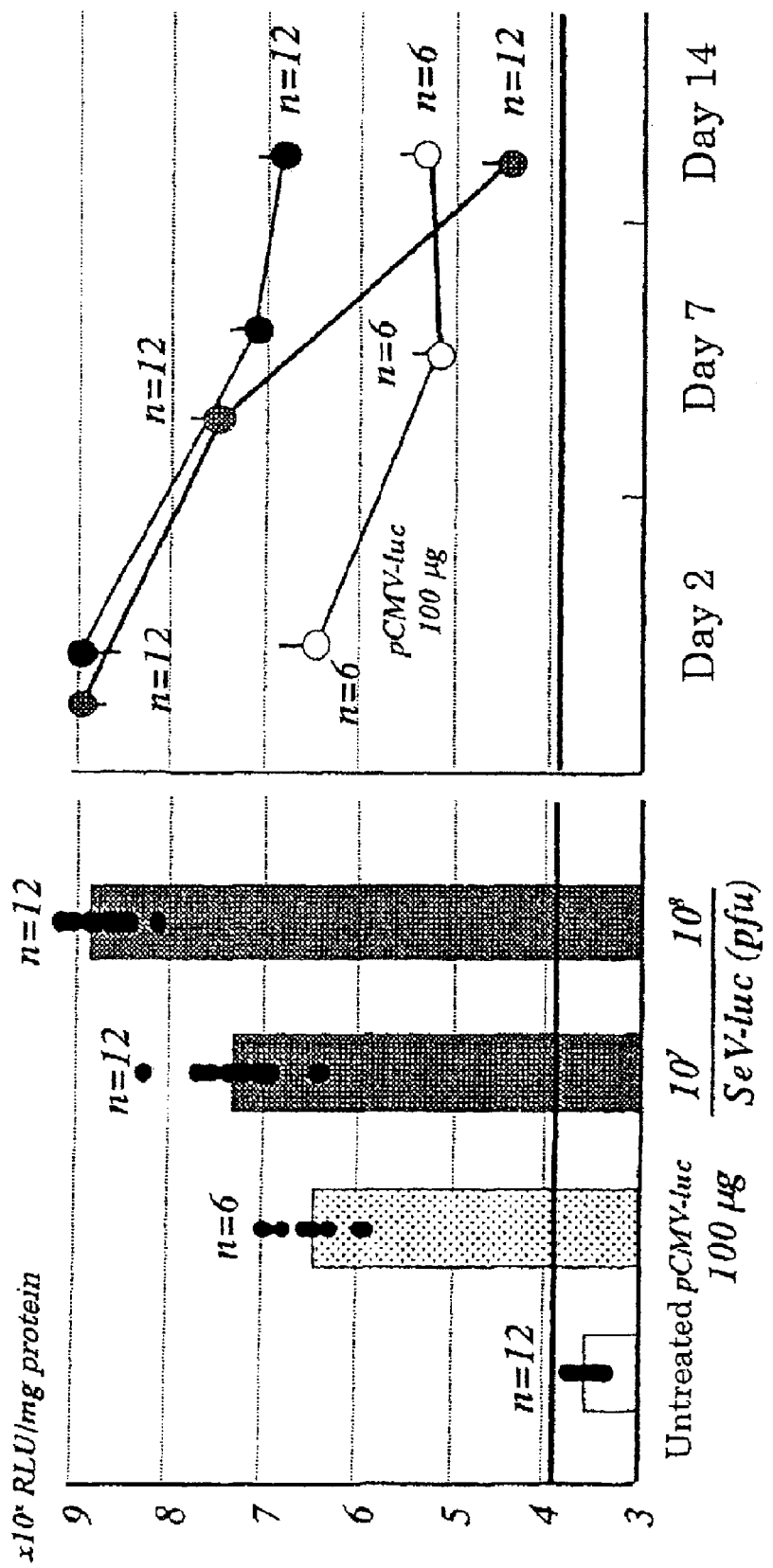
FIG. 4 graphs showing expression level (left) and its time course change (right) of SeV-mediated firefly luciferase gene transferred into muscles. Luciferase activities are examined in the untreated group, the pCMV-luc (100 μg)-administered group, and the SeV-luc ($10^7$ pfu or $10^8$ pfu)-administered group, using moderate ischemia model of C57BL/6 mice (left). The right panel shows the time course changes of the expression level of luciferase gene transferred in the moderate ischemic model. White circles indicate the of pCMV-luc (100-administered C57BL/6 mouse group. Black circles indicate the SeV-luc ($10^8$ pfu)-administered C57BL/6 mouse group. Shaded circles indicate the SeV-luc ($10^8$ pfu)-administered BALB/c nu/nu mouse group. Thick line indicates the cut off-values, above which the expression of the transgene becomes significant. The level of gene expression in each graph is represented in the same log scale.

Kinetics of Recombinant Sendai Virus-Mediated Intramuscular Gene Transfer to Mouse Hind Limb For the kinetic study, the present inventors assessed levels and time course of transgene expression using firefly luciferase. Luciferase assay was carried out using a luminometer (Model LB 9507, EG&G Berthold, Germany) according to literature (Yonemitsu, Y., et al., Nature Biotech. 18, 970-973 (2000)). The data are represented as relative light units (RLU)/mg protein. The concentrations of total proteins were determined by Bradford method using a protein assay system (Bio-Rad Laboratories, Hertfordshire, UK) and were used for standardizing the value obtained by luciferase assay. Since limb muscle of severe limb ischemia model was apparently damaged, suggesting reduced transgene expression, moderate ischemia model (FIG. 1, left panel) were used for analysis. The gene (25 µl) was transferred to two sites, thigh and lower thigh muscles at the time of operation. Doses described herein below are the sum of the doses at two sites. Mice (C57BL/6 mice) that received 100 µg of pCMV-luciferase (about 50 times higher than clinical dose) (Baumgartner, I., et al., Circulation 97, 1114-1123 (1998); Isner, J. M. et al., J. Vasc. Surg. 28, 964-973 (1998)) showed relatively high luciferase activity (mean±S.D.=5.1±3.9×10$^6$ RLU/mg protein, n=6) 2 days after gene transfer, while approximately 5-times (2.4±3.8×10$^7$ RLU/mg protein, n=12) and 120-times (7.3±4.7×10$^8$ RLU/mg protein, n=6) higher expressions were observed in mice that received SeV-luciferase at 10$^7$ Plaque forming units (pfu) and SeV at 10$^8$ pfu, respectively. Further, time course of transgene expression was analyzed using moderate ischemia model of C57BL/6 mice that received luciferase expression plasmid (pCMV-luc) or SeV-luc in the same manner as described above. The moderate ischemia model of C57BL/6 mice that received intramuscular injection of 10$^8$ pfu of SeV-luciferase also showed decline of the expression in time-dependent manner (day 2: 7.3±4.3×10$^8$ RLU/mg protein, n=12; day 7: 3.4±4.7×10$^7$ RLU/mg protein, n=12; and day 14: 2.6±1.2×10$^4$ RLU/mg protein, n=12) (FIG. 4, right panel). Although time course of luciferase activity in the moderate ischemia model of immuno-deficient BALB/c nu/nu mice, to which 10$^9$ pfu of SeV-luciferase were intramusculary administered, was similar to those of the C57BL/6 mice until day 7, the mice kept its expression level later (day 2: 9.4±3.7×10$^8$ RLU/mg protein, n=12; day 7: 1.3±1.9×10$^7$ RLU/mg protein, n=12; and day 14: 0.9±1.3×10$^7$ RLU/mg protein, n=12).

Figure 5:
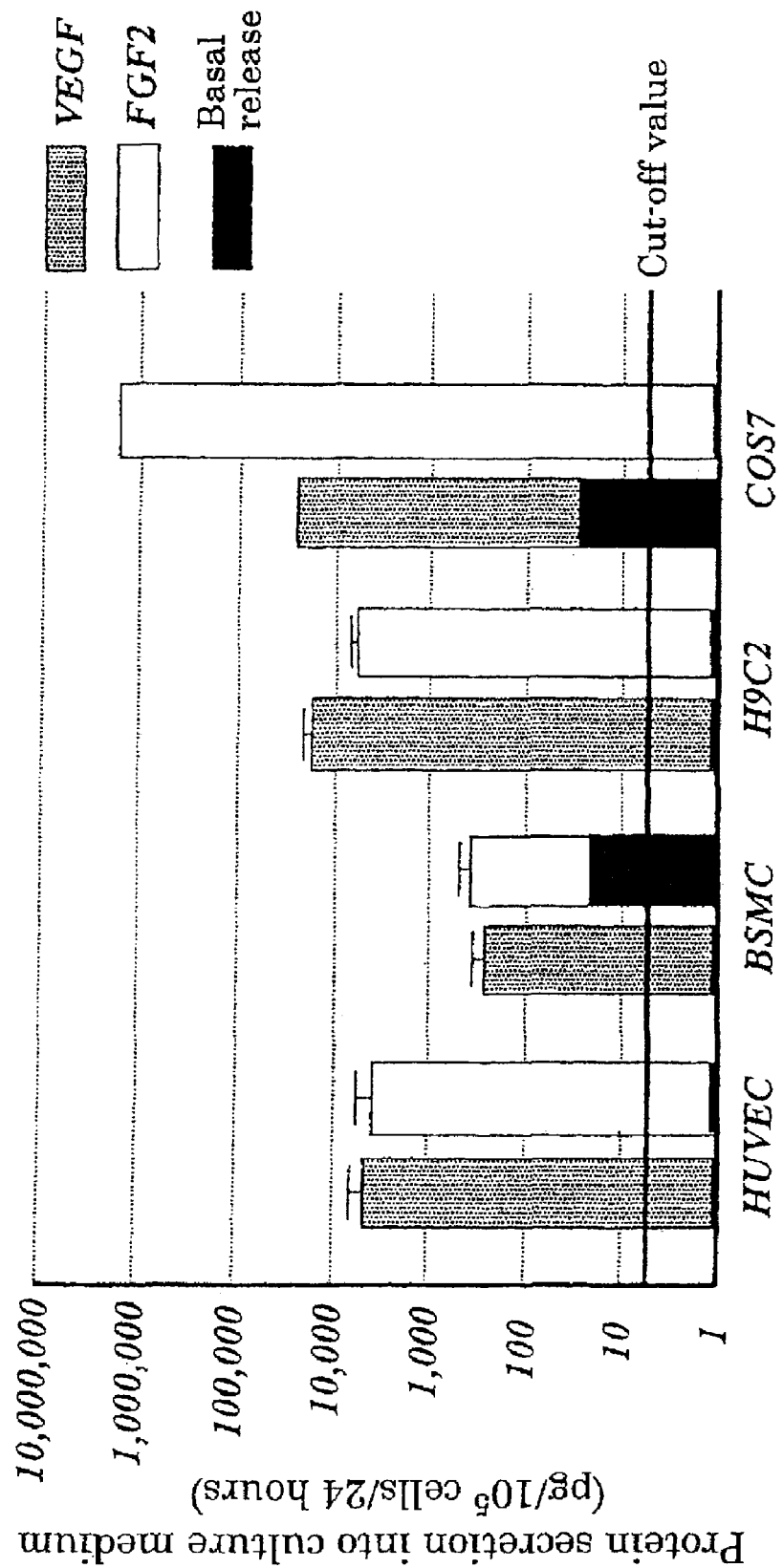
FIG. 5 is a graph showing the secretion level of angiogenic protein in human umbilical vein endothelial cells (HUVEC), COS7 cells, bovine vascular smooth muscle cells (BSMC), and cardiomyoblast cells (H9C2). "Basal release" indicates the production amount of each factor without the vectors. "Cut-off value" indicates the level above which the expression of the transgene becomes significant.

Next, the present inventors assessed secretion of angiogenic proteins in vitro using various culture cells including not only muscular cells such as primary bovine smooth muscle cells (BSMCs) and cardiomyoblasts (H9C2), but also primary human umbilical vein endothelial cells (HUVECs), and COS7 cells. FGF2 vector (SeV-FGF2) which contains no classical signal sequences for secreting proteins was used in the present invention because previous studies by the present inventors and others demonstrated that FGF2 without secreting sequences could be expressed extracellularly (Piotrowicz, R. S. et al., J. Biol. Chem. 272, 7042-7047 (1997); Qu, Z., et al., J. Histochem. Cytochem. 46, 1119-1128 (1998); Florkiewicz, R. Z. et al., J. Cell. Physiol. 162, 388-399 (1995)). As expected, the effective secretion of FGF2 protein into the culture medium could be detected as similar levels of VEGF165 in dose-dependent manner (for example, at MOI=100: VEGF165 vs FGF2=4,354±2,794 vs 3,682±1,063 in HUVEC, 275±58 vs 398±154 in BSMC, 16,987±4,748 vs 5,976±381 in H9C2, and 38,648±4,913 vs 1,547,237±176, 502 in COS7 cells, pg/10$^5$ cells/24 hours, n=3, respectively) (FIG. 5).

Example 3

Kinetics of SeV-Mediated Intramuscular Expression of Angiogenic Factors in Vivo

The present inventors' examined the expression level of angiogenic factors in muscle after in vivo intramuscular administration of SeV-VEGF165 and SeV-FGF2 into moderate ischemia model of C57BL/6 mice. Each 25 µl administration was performed once into the thigh and calf muscles, during operation, using a 26-gauge needle.

Figure 6:
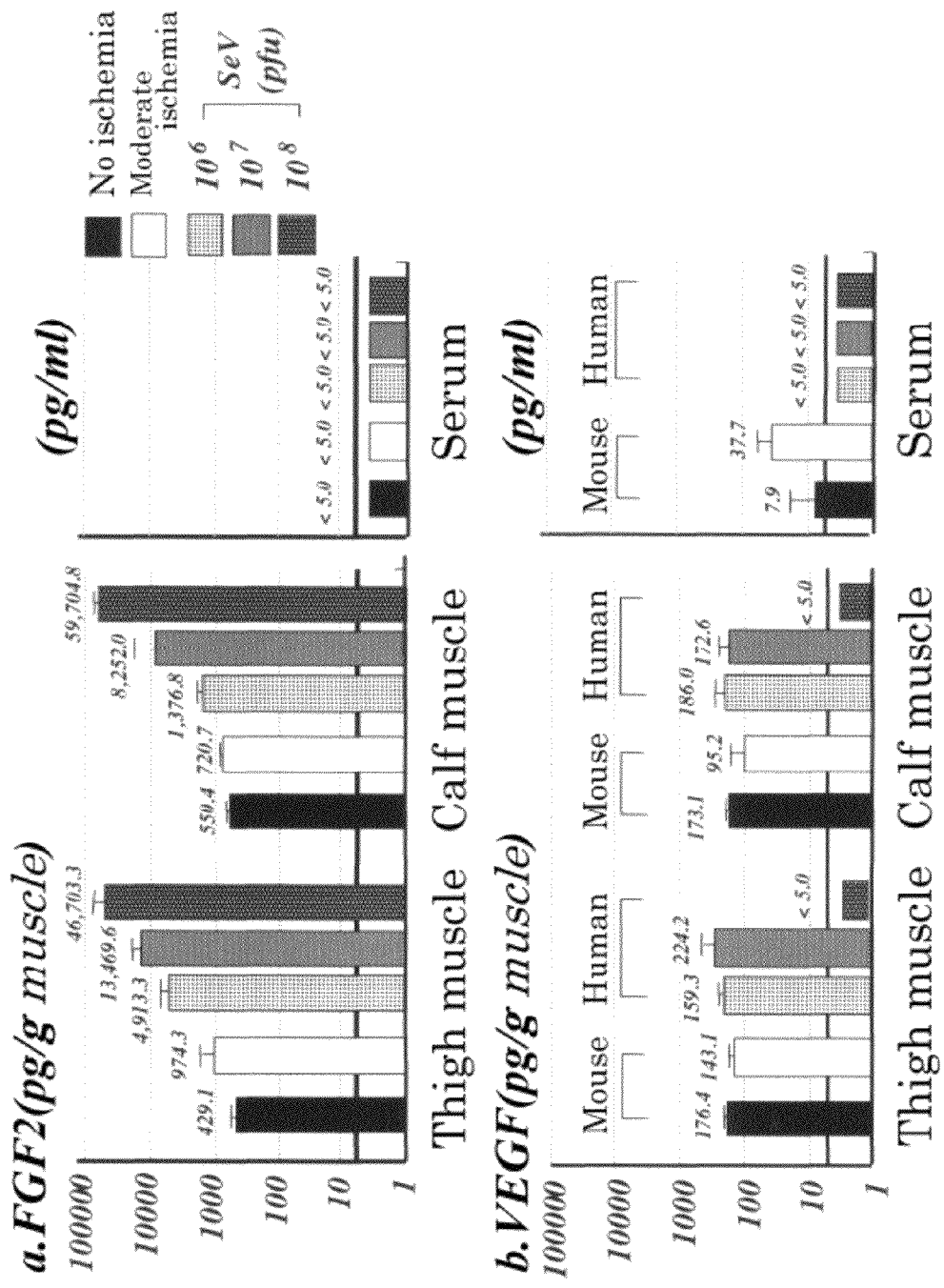
FIG. 6 is graphs showing in vivo expression of exogenously transferred FGF2 (a) and VEGF (b) gene in muscle (left two graphs) and serum (right two graphs) of moderate ischemic limb of C57BL/6 mice. Soon after the operative procedure, 50 μl of each vector solution was injected to thigh and calf muscles. Two days after operation, all thigh and calf muscles (n=6, each) and serum (n=6) were obtained, and subjected to ELISA for murine FGF2 (a) and, murine and human VEGF (b), respectively. Values were standardized by total extracted protein or total volume of muscle and expressed with mean±S.D. Mean values are shown in the figure. Note that the scales are in log scale.

Interesting results were obtained for in vivo expression of angiogenic factors compared to their in vitro expression and in vivo expression of the reporter gene. As shown in FIG. 6, SeV-FGF2-mediated protein synthesis increased in dose-dependent manner reaching 100-fold greater than endogenous gene expression at highest titer (basal line, 429±79, ischemia, 974±150, 10$^6$ pfu, 4,913±313, 10$^7$ pfu, 13,469±12,611, and 10$^8$ pfu, 46,703±12,092 pg/g muscle, n=6 each in thigh muscle; basal line, 550±104, ischemia, 720±128, 10$^6$ pfu, 1,376±158, 10$^7$ pfu, 8,252±8,190, and 10$^8$ pfu, 59,704±35, 297 pg/g muscle, n=6 each in calf muscle). Significant serum FGF2 could not be detected even at highest titer in all animals received SeV-FGF2. On the other hand, dose-dependent increase of VEGF165 was far less than that of FGF2 and did not reach to 2-fold of it at 10$^7$ pfu, and inversely, expression of SeV-derived human VEGF165 protein was almost undetectable at 10⁸ pfu (basal line, 176±44, ischemia, 143±64, 10⁶ pfu, 159±67, 10⁷ pfu, 224±216, and 10⁸ pfu, <5 pg/g muscle, n=6 each in thigh muscle; basal line, 173±45, ischemia, 95±28, 10⁶ pfu, 186±30, 10⁷ pfu, 172±101, and 10⁸ pfu, <5 pg/g muscle, n=6 each in calf muscle). Although serum level of endogenous murine VEGF was significantly increased by moderate limb ischemia (37.7±15.4 µg/ml, n=6), vector-derived human VEGF165 could not be significantly detected, suggesting that intramuscularly expressed VEGF165 did not diffuse to the systemic circulation.

Example 4

Figure 7:
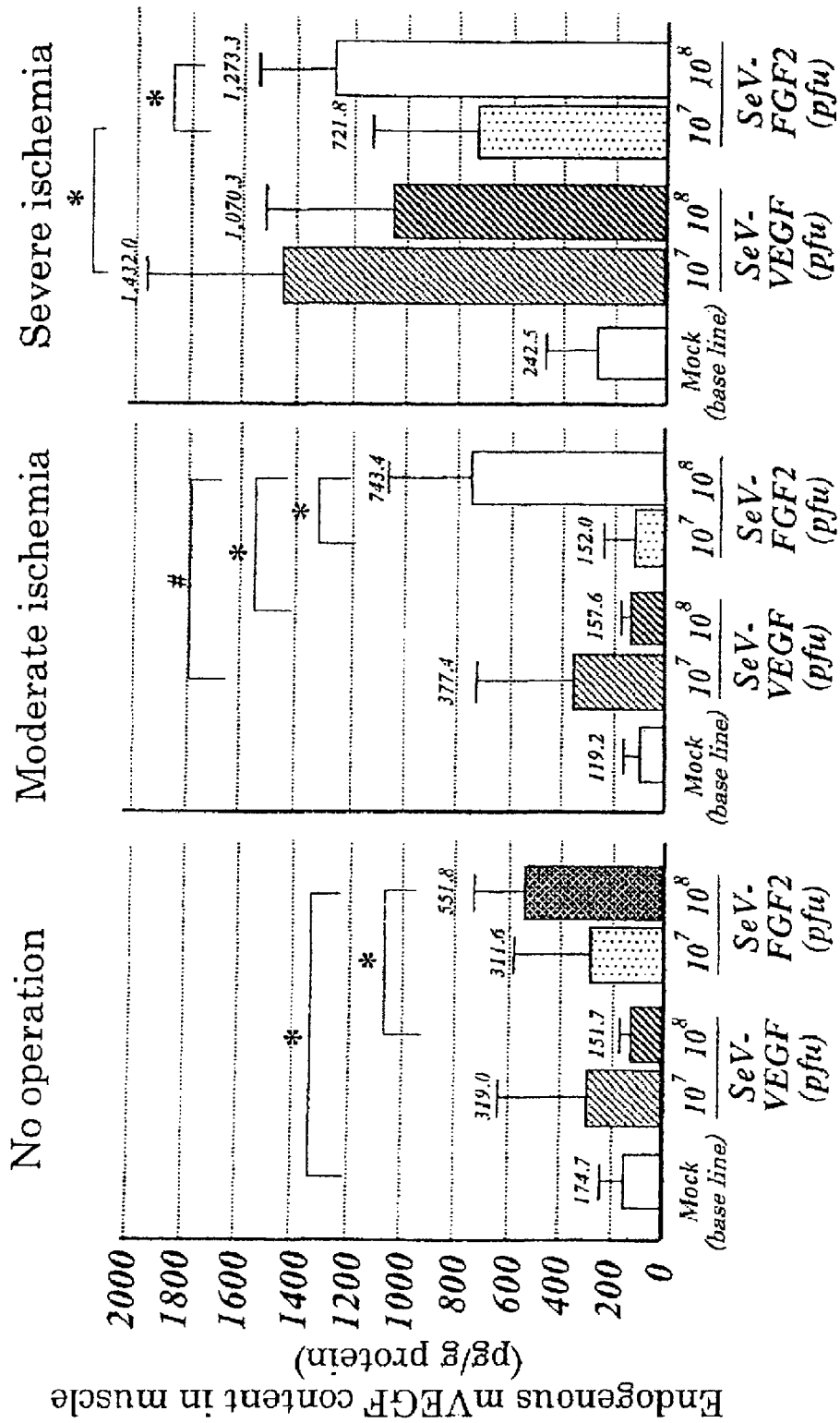
FIG. 7 is graphs showing gene transfer-mediated enhancement of endogenous murine VEGF expression in limb muscles of C57BL/6 mice without operation (left), with moderate ischemia (middle), and severe ischemia (right). Soon after the operative procedure, 50 μl of each vector solution was injected to thigh and calf muscles. Two days after operation, all thigh and calf muscles and serum (n=6 each, total n=12) were obtained, and subjected to ELISA for murine VEGF. Values were standardized by total extracted protein of muscle, and expressed with mean±S.D. Mean values are shown in the figure. *p<0.01, #P<0.05 (analyzed by one-way ANOVA).

Ischemia-Induced Endogenous VEGF Expression is Markedly Enhanced by Angiogenic Gene Transfer The present inventors hypothesized that incomparable expression pattern between VEGF165 and FGF2 is due to endogenous VEGF expression. Overexpression of endogenous VEGF165 may exacerbate tissue ischemia via too much stronger permeability action, and may downregulate the SeV-dependent transcription. Further, a previous report indicated that the angiogenic activity of FGF2 was partly due to enhanced endogenous VEGF expression in vitro and in vivo (Asahara, T., et al., Circulation 92, 365-371 (1995)). Thus, the present inventors assessed modulation of endogenous murine VEGF protein synthesis in muscles via exogenously transduced angiogenic factor genes using murine-VEGF specific ELISA system. As shown in FIG. 7, transfer of FGF2 gene, but not VEGF165 gene, significantly enhanced endogenous murine VEGF levels in muscles in both limb conditions such as normal circulation (no operation) and moderate ischemia. In case of severe limb ischemia, gene transfer of both angiogenic factors, dramatically enhanced endogenous murine VEGF expression, and in particular, VEGF165 resulted in around 7-hold higher than that of ischemia itself (Mock).

Figure 8:
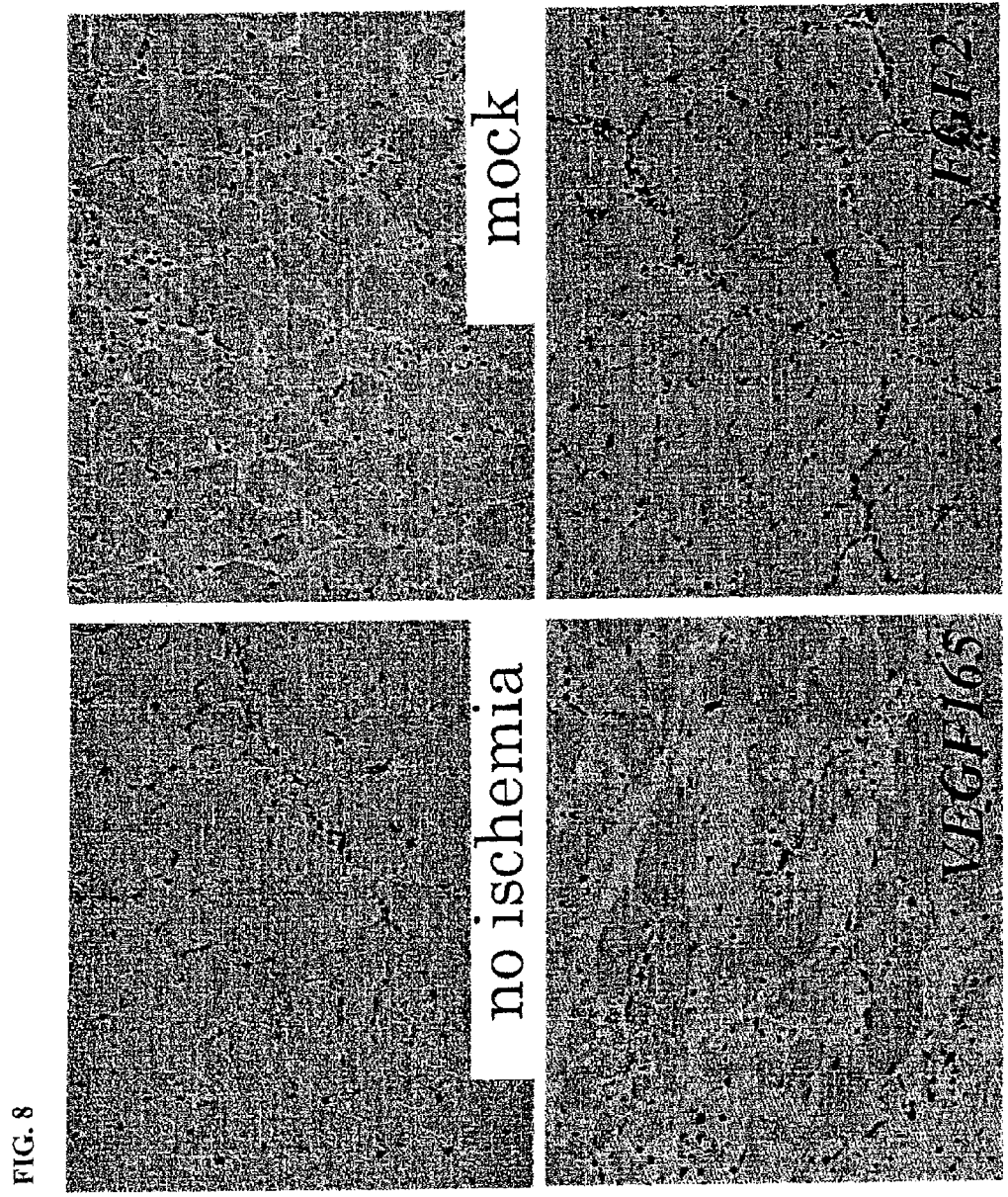
FIG. 8 is photographs showing tissue images of gene-transferred mouse limb muscles. Histological observation was carried out 2 days after severe ischemia operation for C57BL/6 mice, which were then treated as described in the description of FIG. 7. Apparent inflammatory infiltrate and stromal edema can be seen in mock transfected (SeV-luciferase; mock) thigh muscle (upper right), compared to untreated animal (upper left; no ischemia). Severe damage of muscle fibers, intracellular edema, and inflammatory infiltrate can be seen in VEGF165-treated animals (bottom left; VEGF165). These damages are inhibited by FGF2 gene transfer (bottom right; FGF2). Each group contains 6 animals and shows similar results. Hematoxylin-eosin staining. Original magnification ×200.

To assess these further, the present inventors histologically observed effects of gene transfer of angiogenic factors in C57BL/6 severe ischemia model (FIG. 8). Ischemic operation followed by mock transfection (Mock) demonstrated diffusely picnotic muscle fibers associating intracellular edema and inflammatory infiltrate 2 days later. These findings were markedly enhanced by VEGF165 gene transfer, while apparently inhibited by FGF2 gene transfer (FIG. 8).

Example 5

Exogenously Transduced VEGF165 Acts as a Limb Damaging Factor Rather Than Limb Salvaging Factor in Acute Severe Limb Ischemia Based on findings as described above, the present inventors tested therapeutic effects of in vivo gene transfer of angiogenic factors using both moderate and severe ischemic limb models. The present inventors used viruses at 10⁷ pfu for observing in vivo therapeutic effect, because VEGF165 at highest dose of 10⁸ pfu could not produce transgene products as shown above. The present inventors categorized the degree of limb necrosis for 4 salvage scores (Limb Salvage Score: LSS): LSS=4, complete limb salvage; LSS=3, limb necrosis below heel; LSS=2, limb necrosis below knee; LSS=1, limb necrosis above knee; and LSS=0, total limb amputation around the inguinal ligament. According to this classification, the present inventors firstly tested the toxicity of SeV-mediated expression of angiogenic factors using limb salvage model of C57BL/6 mice under severe limb ischemia. The angiogenic genes were transferred in the same manner as in Example 2.

Figure 9:
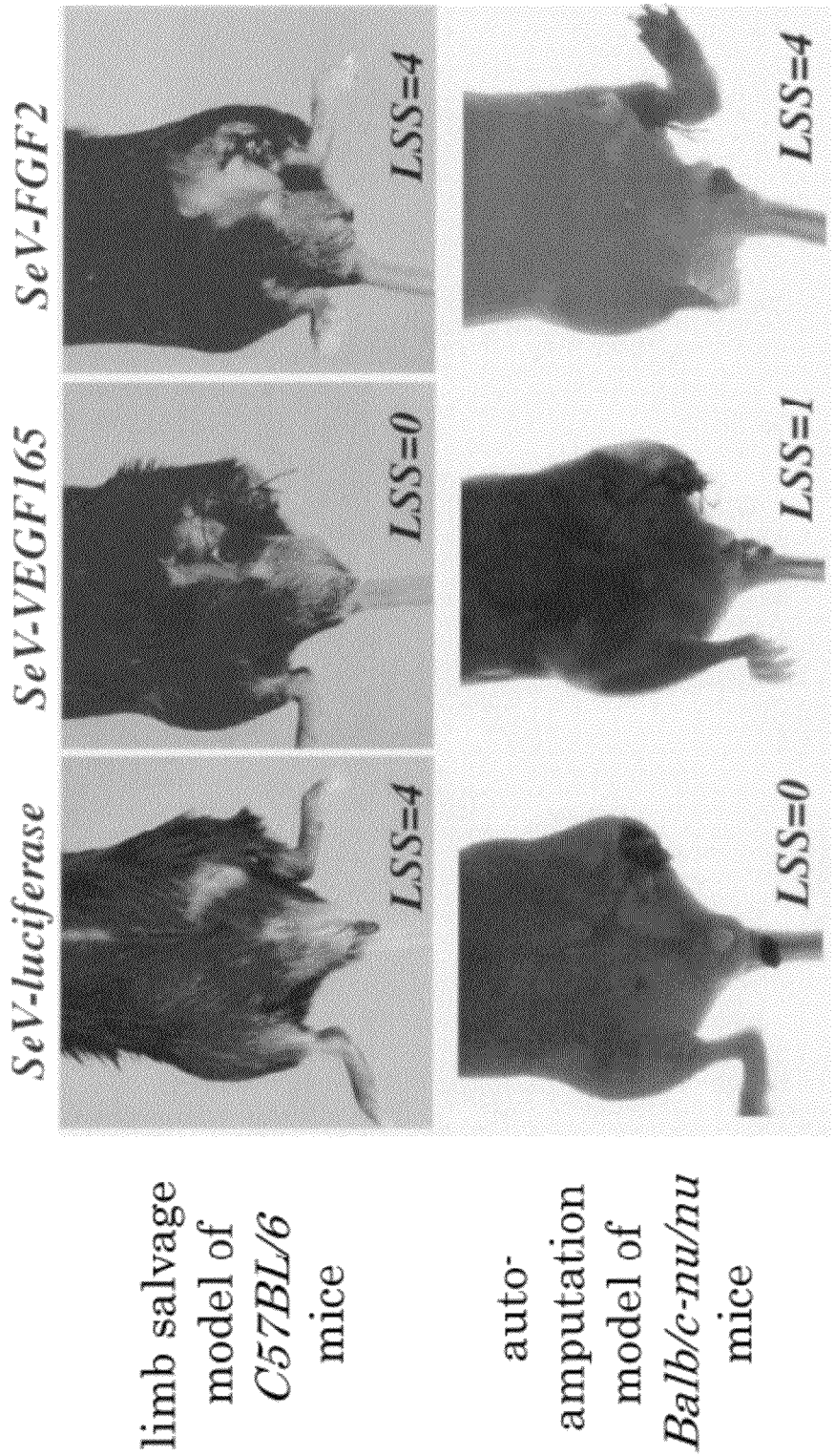
FIG. 9 is photographs showing therapeutic or adverse effects of exogenously transferred angiogenic factor genes in muscles of severe limb ischemia mice 10 days after operation for left hind limbs. Each photograph simultaneously shows limb salvage score (LSS). Upper panels show typical adverse effect in severe ischemia model of C57BL/6 mice (limb salvage model). VEGF165-transferred mouse demonstrated complete limb amputation (upper middle panel), while control mouse with luciferase (upper left panel) and FGF2-treated mouse (upper right panel) indicated salvaged limbs. Lower panels show typical therapeutic effect in severe ischemia model of BALB/c nu/nu mice (auto-amputation model). FGF2-treated mouse demonstrated limb salvage (bottom right panel), while control mouse with luciferase (bottom left panel) and VEGF165-treated mouse (bottom middle panel) indicated almost complete loss of hind limbs.
Figure 10:
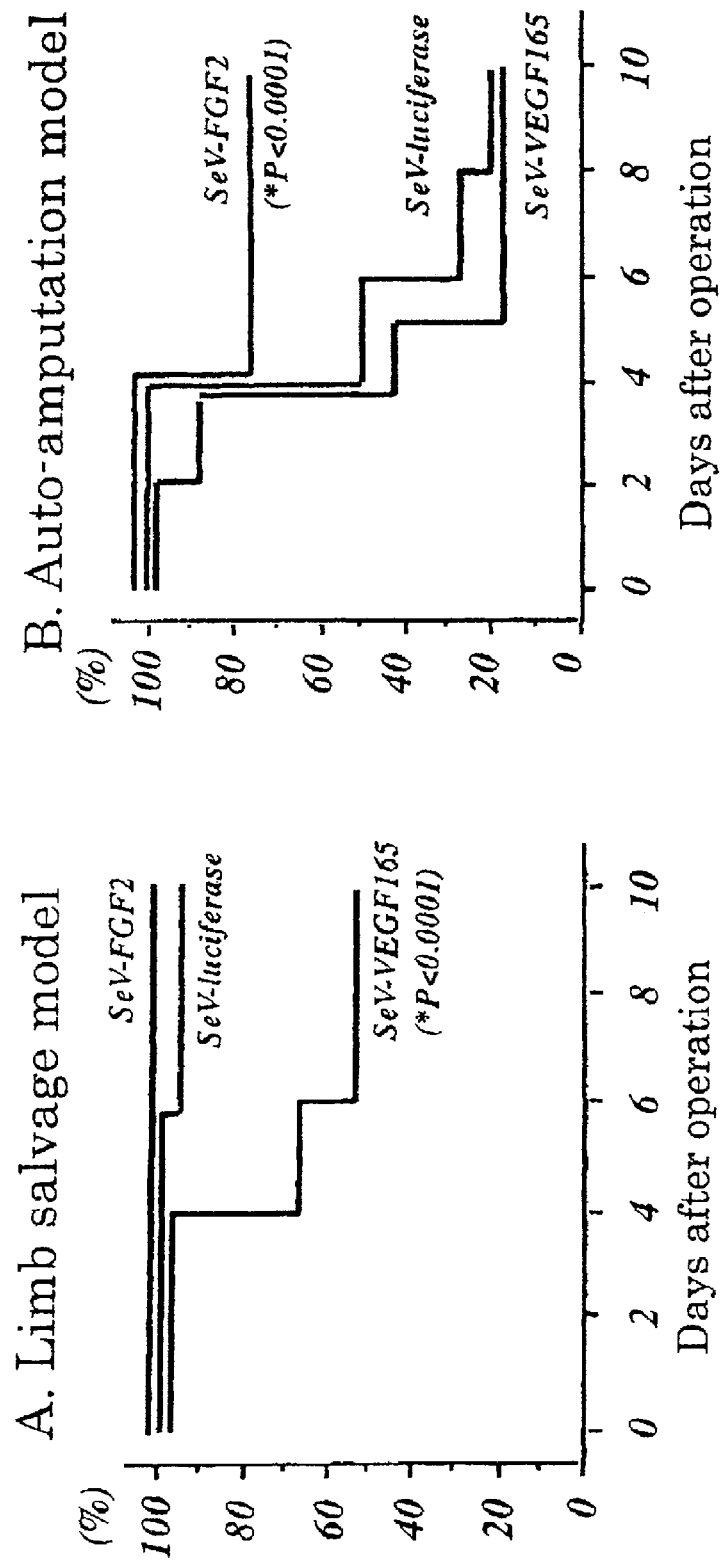
FIG. 10 is graphs showing limb prognosis curve in vector-administered limb salvage and auto-amputation models. The graphs show the rate (limb salvage rate) of vector-administered animals retaining limb. As a result of intramuscular transfer of angiogenic genes, A shows adverse effects of VEGF165 in severe ischemia model of C57BL/6 mice (limb salvage model) and B shows therapeutic effects of FGF2 in severe ischemia model of BALE/c nu/nu mice (auto-amputation model). Each group was subjected to 3 separate experiments (n=10). Curve was described by Kaplen-mayer's method, and data was analyzed with log-rank test. *P<0.0001.

Mice of all groups completely maintained their limbs when vectors were injected thereto two days before ischemia operation. Mice of all groups including FGF2-administered group, except VEGF165-administered group, showed complete limb salvage (% LLS=100%) when vector was injected at the period of operation. As shown in FIGS. 9 and 10, however, some mice that received VEGF165 lost their limbs (5/10 mice lost their limbs, % LLS=52.5%, p<0.0001 compared to other groups) (FIG. 10A). These results suggest limb-damaging effect of VEGF165 gene transfer. Next, the effect of gene therapy with angiogenic genes was analyzed using severe ischemia model (auto-amputation model) of BALB/c nu/nu mice. As a result, administration of SeV-VEGF165 could not improve hind limb prognosis (8/10 lost limbs, % LLS=15.0%) similar to that of luciferase-expressing SeV (5/6 lost limbs, % LLS=16.7%), while administration of SeV-FGF2 significantly inhibited limb amputation in nu/nu mice (2/10 lost limbs, % LLS=77.5%) (FIG. 10B). This indicates apparent limb salvage effect of FGF2 gene transfer.

Figure 11:
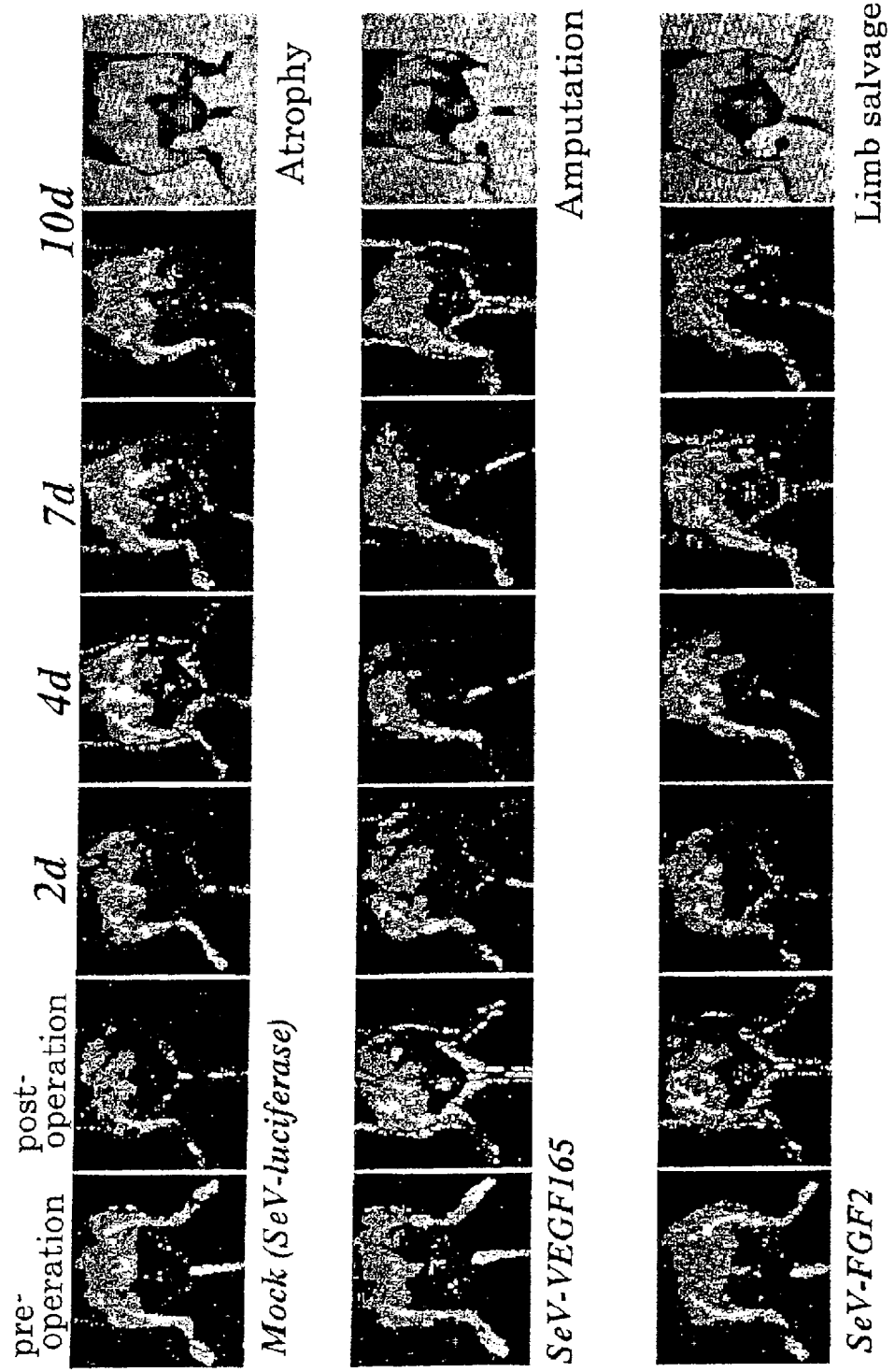
FIG. 11 is photographs showing in vivo angiogenic effect in C57BL/6 mice with severe hind limb ischemia (limb salvage model) measured with a laser Dopplar perfusion image analyzer. Recovery of blood perfusion was observed in the mice treated with SeV-luciferase, SeV-VEGF165, and SeV-FGF2 at $10^7$ pfu. Each group shows the time course of same animal. Upper panels show typical results of time course of blood flow recovery in mouse treated with SeV-luciferase (mock transfection). Blood reperfusion of thigh muscle was recognized around 4 days after intervention, and was apparent at day 7. At day 10, however, no clear perfusion at calf level was hard to be detected, resulting in limb atrophy with a sign of toe necrosis (rightmost panel). Middle panels show typical time course of mouse with SeV-VEGF165. No apparent and significant reperfusion was recognized in thigh and calf during observation, resulting autoamputation of the limb (rightmost panel). Lower panels show typical time course of mouse-treated with SeV-FGF2. Apparent reperfusion at the thigh level was clearly seen until day 4, and significant blood flow was recognized in whole limb until day 10, resulting in complete limb salvage (rightmost panel).

Subsequently, the present inventors determined the effect of intramuscular gene transfer of the recovery of blood perfusion in left limbs subjected to severe ischemia operations, by laser Doppler perfusion image analysis (Couffinhal, T., et al., Am. J. Pathol. 152, 1667-1679 (1998); Murohara, T., et al., J. Clin. Invest. 105, 1527-1536 (2000)). Severe ischemia model (limb salvage model) of C57BL/6 mice were subjected to gene transfer under the same conditions as in the description of FIG. 10A (limb salvage model). Measurements of the ischemic (left)/normal (right) limb blood flow ratio using a laser Doppler perfusion image (LDPI) analyzer (Moor Instruments, Devon, UK) were performed as described previously (Couffinhal, T., et al., Am. J. Pathol. 152, 1667-1679 (1998); Murohara, T., et al., J. Clin. Invest. 105, 1527-1536 (2000)). Specifically, mice were placed on a heating plate kept at 37° C. to minimize data variations due to body temperature before initiating laser scanning. At predetermined time points (before operation and on postoperative days 2, 4, 7, and 10), two consecutive scans were performed over the same region of interest (legs and feet) in each animal (FIG. 11). No essential difference between the two scans was found. After laser scanning, the stored images were subjected to computer-assisted quantification of blood flow, and the average flow of the ischemic and non-ischemic feet were calculated. To minimize data variables due to ambient light and temperature, the LDPI index was expressed as the ratio of left (ischemic) to right (non-ischemic) limb blood flow.

In both mice with SeV-luciferase (Mock) and SeV-FGF2, apparently blood perfusion was detected around upper thigh at day 4, and particularly, significant perfusion into the calf muscle was seen in the FGF-administered group at day 4, 7, and 10, compared to limited perfusion in the thigh muscle in luciferase-administered group at the same time points (FIG. 11). As representative results, some of luciferase-injected mice showed moderate atrophic limbs, while FGF2-injected mice largely showed undamaged limbs. In contrast, mice received VEGF165 revealed very low blood perfusion in thigh muscle, resulting limb amputation (FIG. 11). All mice received SeV-VEGF165 had lost their limbs at least knee level. The observation results of limb blood perfusion in each administration group are described below.

1. SeV-Luciferase-Administered Individuals

Blood perfusion in the left lower limb was hardly observed immediately after operation. Blood perfusion was gradually recovered and by 4 days after operation it was recovered up to approximately the middle of the femoral region. However, blood perfusion into the lower thigh had not recovered by 10 days after operation. As a result, the lower limb did not have necrosis but showed atrophy to some extent as shown in the rightmost panel. The same result was observed in one third of the individuals. Some individuals showed better recovery than other individuals did as described above.

2. SeV-VEGF165-Administered Individualsed

As described above, most of the blood perfusion was diminished right after operation. Further periodical observation could hardly find the recovery of blood perfusion in the femoral region. As a result, the lower limb from middle of the femoral region was auto-amputated as shown in the rightmost panel. All 10 individuals showed completely the same result.

3. SeV-FGF2-Administered Individuals

As described above, most of the blood perfusion in the left lower limb was diminished right after operation. The region where blood perfusion was diminished was about the same as the SeV-luciferase-administered individual. Strong blood perfusion (indicated by red spots) was observed in the femoral region at about day 4 and weak blood perfusion in the lower limb was already observed at day 7. Slight but significant blood perfusion (indicated in blue) throughout the left lower limb was observed at day 10. As a result, the lower limb was maintained as it was normal in appearance as shown in the rightmost panel.

Figure 12:
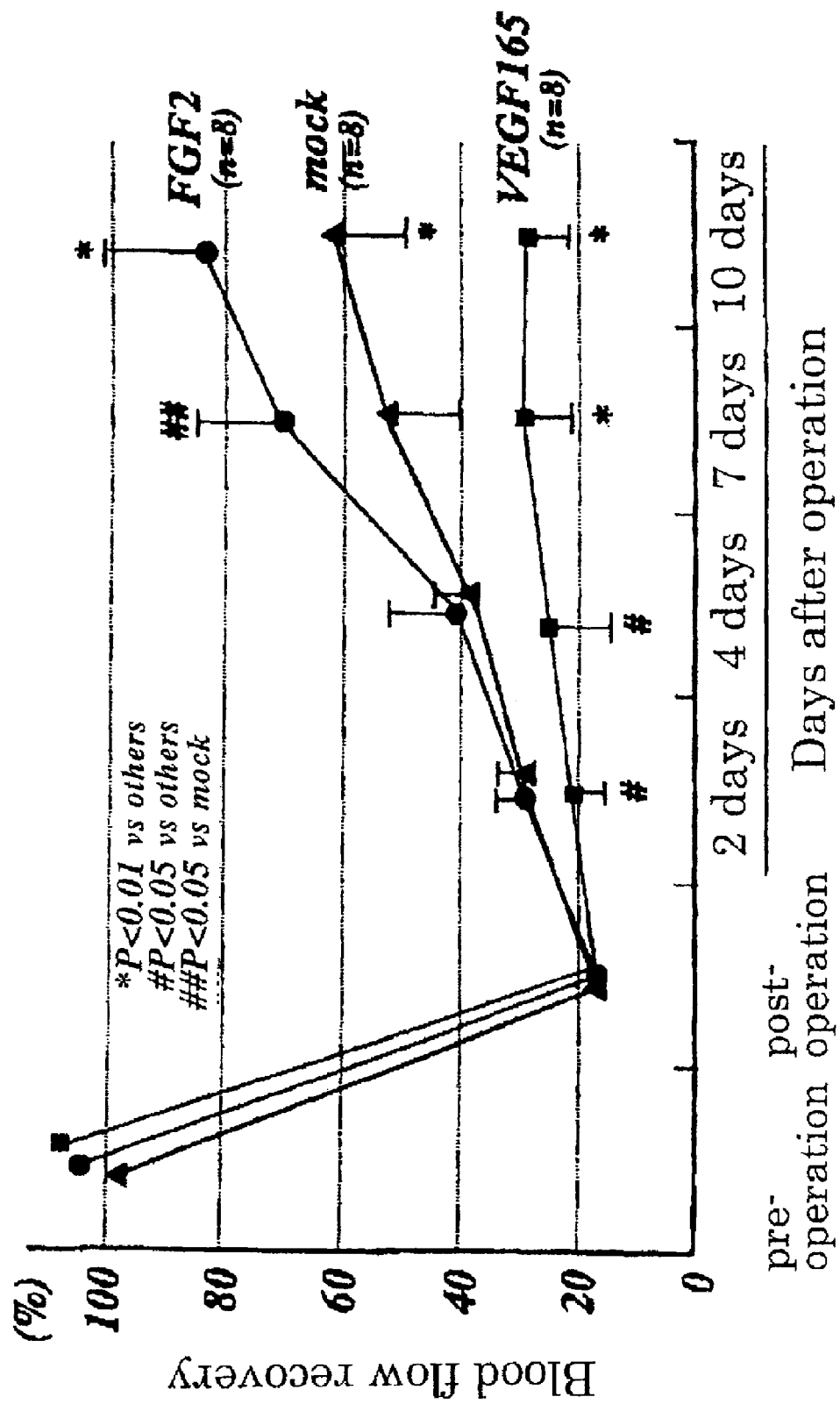
FIG. 12 is a graph showing the recovery of blood perfusion by angiogenic gene therapy in C57BL/6 mice with severe ischemia (limb salvage model). The average blood perfusion in the ischemic limb and control limb treated as in the description of FIG. 11 was calculated to give the blood perfusion value ratio, of left limb (ischemic)/right limb (control). *P<0.001 (compared with all other groups), #p<0.05 (compared with all other groups), ##p<0.05 [compared with non-administered (mock) group].

The present inventors statistically compared Dopplar image-based blood flow in thigh muscle of each groups. As shown in FIG. 12, mice received SeV-FGF2 showed significantly higher blood perfusion than those received SeV-luciferase with physiological recovery of limb circulation. In contrast, blood flow in thigh muscle of mice treated with SeV-VEGF165 remained low, and after 7 days post operation many of them lost their limbs at least knee level.

Example 6

Therapy of Acute Ischemic Limb Using Replication Ability-Deficient Sendai Virus Vector 1. Construction of F Gene-Deficient Sendai Virus Genome cDNA Containing Angiogenic Genes First, amplification of the EGFP gene was performed by PCR to construct the plasmid (pSeV18+/ΔF-GFP) containing the EGFP gene at the F gene-deficient site in the plasmid pSeV18+/ΔF (see WO00/70055 and WO00/70070), which was prepared by deleting the F gene of the plasmid pSeV18+ b(+) (Hasan, M. K. et al., J. Gen. Virol. 78, 2813-2820, 1997) containing full-length Sendai virus (SeV) genomic cDNA. PCR was performed using NisI-tailed primer (5'-atgcatatggt-gatgcggttttggcagtac/SEQ ID NO: 9) for 5' end and NgoMIV-tailed primer (5'-tgccggctattattacttgtacagctcgtc/SEQ ID NO: 10) for 3' end to adjust the number of nucleotides of the EGFP gene fragment to be a multiple of 6 (Hausmann, S. et al., RNA 2, 1033-1045, 1996). The PCR product was digested with restriction enzymes NsiI and NgoMIV and a fragment was recovered from a gel and subcloned into the F gene-deficient region in pUC18/dFSS between NsiI and NgoMIV and sequencing was performed for confirmation. The EGFP gene-containing DraIII fragment isolated from this vector was replaced with the DraIII fragment of pSeV18' containing the F gene, and ligated to construct pSeV18+/ΔF-GFP. However, even though the downstream ORF of the F gene is removed from pSeV18+/ΔF, the EIS sequence (SeV specific sequence, E: end, I: intergenic, S: start) of the F gene remains causing the possible expression of a 5 amino acid peptide derived from the primer which is used to connect the fragment into the vector. Moreover, since GFP is coexpressed in pSeV18+/ΔF-GFP, a vector which did not coexpress GFP and the 5-amino-acid peptide was constructed. The recombination was performed to construct the vector as follows.

The fragment (6288 bp) containing the F gene-deficient region was recovered by digesting pSeV18+/ΔF-GFP with SalI and NheI and cloned into Litmus38 (New England Biolabs, Beverly, Mass.) to construct LitmusSalINheIfrg/ΔF-GFP. The deletion of the EGFP gene containing the EIS sequence located upstream of the F gene-deficient region was performed by Inverse PCR. Specifically, PCR was performed using a reverse primer (5'-gtttaccaggtggagagttttgcaac-caagcac/SEQ ID NO: 11) which was designed to contain a restriction enzyme SexAI recognition sequence in upstream of GFP gene and a forward primer (5'-ctttcacctggtacaagcaca-gatcatggatgg/SEQ ID NO: 12) which was designed to contain the restriction enzyme SexAI recognition sequence in downstream of GFP gene. The desired sized fragment (10855 bp) was isolated and ligated to delete the EGFP gene containing the EIS sequence located upstream of the F gene-deficient region.

In this construct, the extra 15-bp sequence is inserted between SexAI sites due to the design of the primers. Therefore, the plasmid was prepared by transforming into E. coli SCS110 strain (dcm−/dam− SCS110 strain was used because SexAI was methylated and could not be digested). Two DNA fragments, 1628 bp and 9219 bp, were recovered after digesting with SexAI, and ligated to remove the extra 15-bp fragment. Finally, LitmusSalINheIfrg/ΔF (Δ5aa) was constructed, in which the EGFP gene containing the EIS sequence located upstream of the F gene and consisting of a multiple-of-6 number of nucleotides was deleted. After the plasmid was digested with SalI and NheI, the resulting fragment was recovered, replaced with a SalI/NheI fragment which contained the F gene of pSeV 18', and ligated to construct plasmid pSeV18"/ΔF (Δ5aa). Insertion of the angiogenic gene (for example, human FGF2 gene) into the plasmid was performed as follows using the restriction enzyme NotI recognition sequence located upstream of the NP gene.

2. Construction of F Gene-Deficient Sendai Virus Genome cDNA Encoding hFGF2

Human FGF2 (hFGF2) cDNA was obtained by RT-PCR from vascular smooth muscle cells isolated from human great saphenous artery with the consent of the subject and thereby subcloning the PCR product into pBluescriptSK+ (Stratagene, La Jolla, Calif.) at HindIII (5' end) and EcoRI (3' end) sites. At the same time, the hFGF2 cDNA sequence was confirmed to be identical to the reported sequence by Abraham et al. (Abraham, J. A. et al., EMBO J. 5 (10), 2523-2528, 1986).

In order to insert the hFGF2 gene at the restriction enzyme NotI site located upstream of the NP gene in pSeV18+/ΔF (Δ5aa), a SeV specific sequence (EIS sequence) was added at the 3' end of the hFGF2 gene and the fragment containing a NotI recognition sequence at both ends was prepared. Specifically, PCR was performed using the hFGF2 cDNA described above as a template and using N-terminus primer (5'-atccgcggccgccaaagttcacttatg-gcagccgggagcatcaccacgctgc-ccgccttgcccgaggatggcggcagcggcgcc/SEQ ID NO: 13) containing a start codon and C-terminus primer (5'-atccgcggccgcgatgaactttcaccctaagttttcttactacggtcagctcttagca gacattggaagaaaaagtatagc/SEQ ID NO: 14) containing a stop codon and the EIS sequence. The PCR product was digested with NotI and then subcloned into pBluescriptSK+ (Stratagene, La Jolla, Calif.) at a NotI site to obtain pBS-hFGF2. The nucleotide sequence of pBS-hFGF2 was confirmed.

The fragment containing hFGF2 cDNA was obtained by digesting pBS-hFGF2 with NotI and subcloned into pSeV18$^+$/ΔF (Δ5aa) at a NotI site located upstream of the NP gene to construct F gene-deficient Sendai virus genomic cDNA containing the hFGF2 gene, pSeV18$^+$hFGF2/ΔF (Δ5aa) (pSeV18$^+$hFGF2/ΔF (Δ5aa) is also indicated as pSeV18$^+$hFGF2/ΔF). Moreover, NotI fragment containing hFGF2 cDNA was inserted at NotI site in pSeV18$^+$b(+) encoding virus cDNA with replication ability to construct pSeV18$^+$hFGF2 Replicative SeV vector expressing human FGF2 was prepared from pSeV18$^+$ hFGF2 by the known method (Hasan, M. K. et al., J. Gen. Virol. 78: 2813-2820, 1997; Kato, A. et al., 1997, EMBO J. 16: 578-587; Yu, D. et al., 1997, Genes Cells 2: 457-466) to construct SeV-hFGF2.

3. Reconstruction and Amplification of F Gene-Deficient Sev

Reconstruction of F gene-deficient SeV vector using F-expressing helper cells (LLC-MK2/F; see WO00/70055 and WO00/70070) which inducibly expressed the Sendai virus F gene (SeV-F) by Cre DNA recombinase was performed (the cells before the induction of SeV-F gene expression are referred to as LLC-MK2/F and the cells after that as LLC-MK2/F/Ad). LLC-MK2 cells were seeded onto 10-cm Petri dish in diameter at $5 \times 10^6$ cells/dish, incubated for 24 hours, and then transfected for 1 hour (moi=2) with T7 RNA polymerase-expressing recombinant Vaccinia virus (Fuerst, T. R. et al., Proc. Natl. Acad. Sci. USA 83, 8122-8126, 1986) which were treated with solaren and long wave ultra violet light (365 mm) for 20 min. UV Stratalinker 2400 (Catalog Number 400676 (100 V), Stratagene, La Jolla, Calif., USA) equipped with five 15-watt bulbs was used for UV exposure to Vaccinia virus. Cells were then washed twice. Plasmids pSeV18$^+$ hFGF2/ΔF, pGEM/NP, pGEM/P, pGEM/L (Kato, A. et al., Genes Cells 1, 569-579, 1996), and pGEM/F—HN (WO00/70070) were resuspended in OptiMEM (GIBCO) at concentration of 12 μg, 4 μg, 2 μg, 4 μg, and 4 μg per dish, respectively, and then mixed with SuperFect transfection reagent (1 μg DNA/5 μl of SuperFect, QIAGEN). The mixtures were left at room temperature for 15 min, mixed with 3 ml OptiMEM containing 3% FBS, and then added to the cells. The cells were incubated for 3 to 5 hours, washed with serum-free MEM twice, and further incubated in serum-free MEM containing 40 μg/ml cytosine β-D-arabinofuranoside (AraC, Sigma) and 7.5 μg/ml trypsin (GIBCO) for 24 hours.

The culture medium was removed from the cell cultures and the F-expressing helper cell LLC-MK2/F/Ad cells cloned as described above were layered on top of the cells. Specifically, LLC-MK2/F/Ad cells suspended in serum-free MEM (containing 40 μg/ml AraC and 7.5 μg/ml trypsin) were layered on top of the cells in which the culture medium had been removed, and then the cells were incubated for 48 more hours. The cells were recovered by scraper and pellets were resuspended in OptiMEM ($10^7$ cells/ml) and freeze-thawed 3 times. This lysates (200 μl/well) were layered on top of LLC-MK2/F/Ad cells ($4 \times 10^6$ cells/well of 12-well plate), 300 μl/well of serum-free MEM (containing 40 μg/ml AraC and 7.5 μg/ml trypsin) was added thereto, and the cells were incubated for 15 to 24 hours. The culture medium was removed and cells were washed with serum-free MEM. A fresh serum-free MEM (containing 40 μg/ml AraC and 7.5 μg/ml trypsin) was added to the cells and then incubated for 5 to 9 days, and culture medium was collected. The collected culture medium was used to infect LLC-MK2/F/Ad cells and the cells were incubated as described above in serum-free MEM (containing 40 μg/ml AraC and 7.5 μg/ml trypsin) to amplify F gene-deficient SeV.

At the same time, the culture medium containing F gene-deficient SeV particles was passed twice through a 0.22 μm filter to remove contaminating recombinant Vaccinia virus used for T7 RNA polymerase expression during the reconstruction. Specifically, the culture medium (sample after P2) amplified at least twice with serum-free MEM containing AraC (containing 40 μg/ml AraC and 7.5 μg/ml trypsin) was passed twice through a 0.22 μm filter. Furthermore, the culture medium amplified once with serum-free. MEM containing AraC (containing 40 μg/ml AraC and 7.5 μg/ml trypsin) was recovered to obtain F gene-deficient SeV (SeV-hFGF2/ΔF) which was amplified without contamination of recombinant Vaccinia virus.

Figure 13:
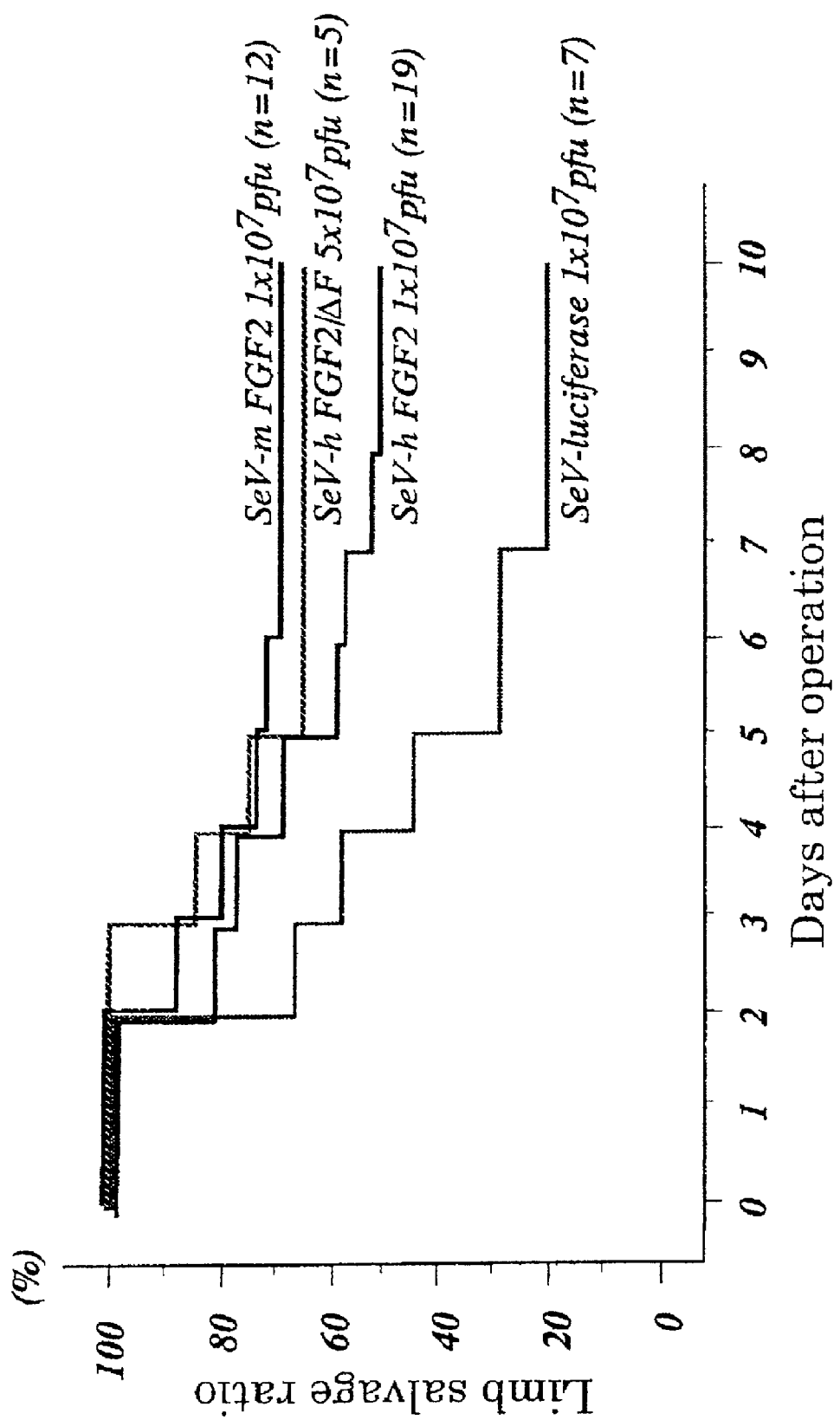
FIG. 13 is a graph showing time course change in limb salvage ratios in mouse severe ischemia models (auto-amputation model) to which the F gene-deficient SeV vector containing the hFGF2 gene or replicative SeV vector containing the hFGF2 gene. In the figure, the number of subjects (n) and the dose of vectors are shown.

4. Gene Therapy for Ischemic Limb Using Replicative and Non-Replicative Human FGF2 Expression SeV Vector The present inventors assessed the treatment effect by administration of replicative and non-replicative human FGF2 expression SeV vector using severe ischemia model of BALB/c nu/nu mice (auto-amputation model) described in Example 1. Angiogenic gene transfer was carried out in the same manner as in Example 2. The vectors were injected during operation. Limb amputation after operation was observed and the limb salvage ratio (ratio of the number of individuals which kept limbs to the total number of animals) at each period was calculated (FIG. 13).

Control mice that received luciferase expression SeV (SeV-luciferase) showed a high limb amputation ratio, similar to the non-administered mice. In contrast, limb amputation was significantly suppressed in mice that received human FGF2 expression vector (SeV-hFGF2 and SeV-hFGF2/ΔF). This experiment revealed that human FGF2-expressing Paramyxovirus vector is highly effective as an angiogenic gene transfer vector to treat ischemic diseases, and that non-replicative Paramyxovirus vector is effective for ischemia treatment.

Example 7

Therapeutic Effect of SeV-FGF2 Gene Transfer for Cardiac Infarction Mice

Figure 14:
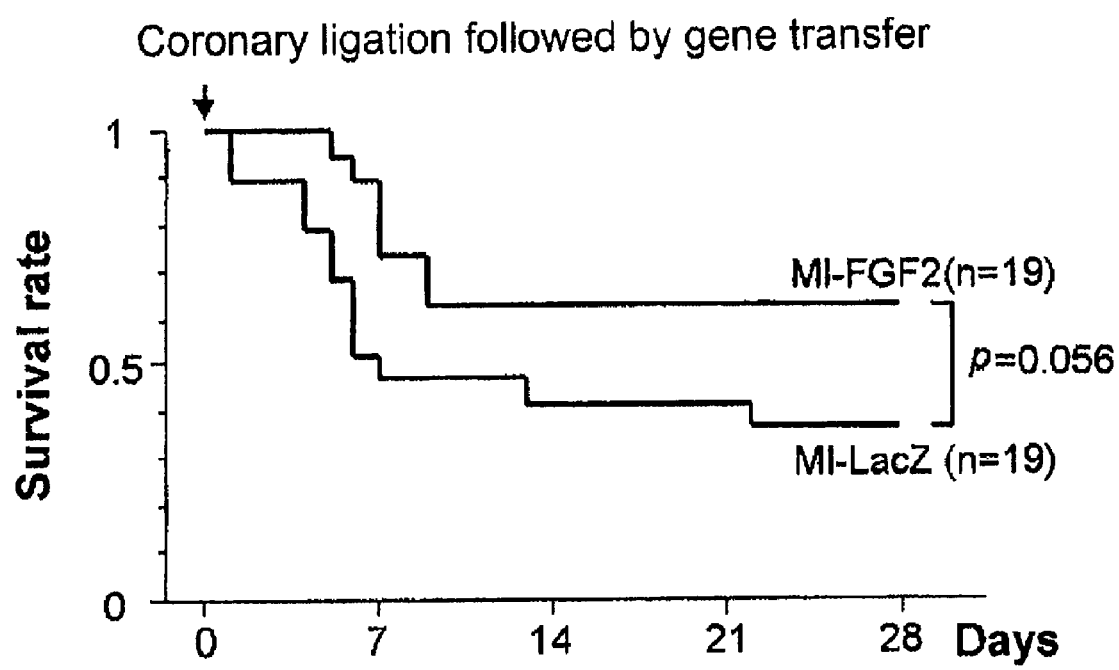
FIG. 14 shows the therapeutic effect of SeV vector containing FGF2 gene in mice (cardiac infarction model) whose coronary artery is ligated.

FGF2 gene transfer with SeV-FGF2 following coronary artery ligation was conducted as follows. Mice (C57BL/6J, male, 8 w to 10 w, and 22 g to 26 g (average 23.5 g)) were maintained by artificial respiration after endotracheal intubation under anesthesia by i.p. administration of Pentobarbital. Thoracotomy was performed through the left 4$^{th}$ intercostal after skin incision at the left precordium. The left coronary artery was ligated at two sites of the left auricular level using 8-0 silk thread. The vectors (SeV-FGF2 or SeV-LacZ) were directly injected at a total of 10 sites including the left ventricle infarction areas (2 sites), borderline areas (5 sites), and non-infarction areas (3 sites) using an injection needle having approximately 0.15 mm in outer circumference and about 0.5 mm in length. 5 μl of the vector, which was diluted 50 fold with PBS, was injected at each site, namely a total of 50 μl ($1 \times 10^6$ pfu) of the vector was injected. The chest was closed by suturing the intercostal, followed by skin suture. Extubation was done after consciousness and the respiratory condition were stabilized. The mice were maintained in a warm environment after operation. The time duration from intratracheal intubation to skin suture was 50 min. Fatality was approximately 15% to 20% on the day of operation (including fatality during operation). As shown in FIG. 14, a significant therapeutic effect was observed in individuals that received Sendai virus vectors expressing FGF2 compared with the individuals that received with Sendai virus expressing lacZ.

What is claimed is:

1. A method for inducing angiogenesis in a subject in need thereof, said method comprising the step of administering to said subject an angiogenic composition comprising a pharmaceutically acceptable carrier and a Paramyxovirus vector comprising a gene encoding fibroblast growth factor 2 (FGF2), thereby inducing angiogenesis in said subject.

2. The method of claim 1, wherein said angiogenic composition comprises a cell comprising said Paramyxovirus vector.

3. The method of claim 1, wherein said angiogenic composition is intramuscularly injected.

4. The method of claim 1, wherein said angiogenesis is induced in an ischemic limb in said subject.

5. The method of claim 1, wherein said Paramyxovirus is Sendai virus.

6. The method of claim 5, wherein said angiogenic composition comprises a cell comprising said Paramyxovirus vector.

7. The method of claim 5, wherein said angiogenic composition is intramuscularly injected.

8. The method of claim 1, wherein said Paramyxovirus vector lacks the F gene.

9. The method of claim 8, wherein said angiogenic composition comprises a cell comprising said Paramyxovirus vector.

10. The method of claim 8, wherein said angiogenic composition is intramuscularly injected.

11. The method of claim 1, wherein said subject is human.

12. A method of treating ischemic tissues in a subject in need thereof, said method comprising the step of administering to said subject an angiogenic composition comprising a pharmaceutically acceptable carrier and a Paramyxovirus vector comprising a gene encoding fibroblast growth factor 2 (FGF2), wherein said method induces angiogenesis in said subject, thereby treating said ischemic tissues in said subject.

13. The method of claim 12, wherein said angiogenic composition comprises a cell comprising said Paramyxovirus vector.

14. The method of claim 12, said angiogenic composition is intramuscularly injected.

15. The method of claim 12, wherein said angiogenesis is induced in an ischemic limb in said subject.

16. The method of claim 12, wherein said Paramyxovirus is Sendai virus.

17. The method of claim 16, wherein said angiogenic composition comprises a cell comprising said Paramyxovirus vector.

18. The method of claim 16, wherein said angiogenic composition is intramuscularly injected.

19. The method of claim 12, wherein said Paramyxovirus vector lacks the F gene.

20. The method of claim 19, wherein said angiogenic composition comprises a cell comprising said Paramyxovirus vector.

21. The method of claim 19, wherein said angiogenic composition is intramuscularly injected.

22. The method of claim 12, wherein said subject is human.

* * * * *

UNITED STATES PATENT AND TRADEMARK OFFICE
CERTIFICATE OF CORRECTION

| | | |
|---|---|---|
| PATENT NO. | : 8,211,868 B2 | Page 1 of 1 |
| APPLICATION NO. | : 13/049011 | |
| DATED | : July 3, 2012 | |
| INVENTOR(S) | : Yoshikazu Yonemitsu et al. | |

It is certified that error appears in the above-identified patent and that said Letters Patent is hereby corrected as shown below:

Cover page, under item (75) Inventors, replace

"Masayuki Fukumura, Ikeda (JP);" with --Masayuki Fukumura, Osaka (JP);--;

"Mamoru Hasegawa, Tsukuba (JP);" with --Mamoru Hasegawa, Ibaraki (JP);--.

Cover page, under OTHER PUBLICATIONS, line 3, in Asahara et al.," replace

"ll365-371, 1995." with --365-371, 1995.--.

Page 2, Col. 1, line 26, in Kalke et al., replace "Kalke" with --Kalka--;

Col. 1, line 27, in Kaneda et al., replace "Japanse" with --Japanese--;

Col. 2, line 9, in Pettersson et al., replace "Heterogenetiy" with --Heterogeneity--;

Col. 2, line 25, in Sakai et al., replace "Accomodation" with --Accommodation--;

Col. 2, line 32, in Seghezzi et al., replace "Angiogensis" with --Angiogenesis--.

Column 1, Line 64, replace "angiomatousid" with --angiomatous--.

Column 7, Line 24, replace "angiogic gene" with --angiogenic gene--;

Line 33, replace "intramusculary" with --intramuscularly--.

Column 11, Line 47, replace "deletin of the genes" with --deletion of the genes--.

Column 15, Line 28, replace "intracellulary," with --intracellularly,--.

Column 23, Line 9, replace "transgenelocally" with --transgene locally--.

Column 31, Line 3, replace "VEGF may leaked" with --VEGF may have leaked--.

Column 35, Line 8, replace "Individualsed" with --Individuals--.

Column 37, Line 15, replace "Sev" with --SeV--.

Signed and Sealed this

Twenty-ninth Day of January, 2013

David J. Kappos
*Director of the United States Patent and Trademark Office*